United States Patent
Almansa-Rosales

(10) Patent No.: US 10,508,114 B2
(45) Date of Patent: Dec. 17, 2019

(54) SPIRO-ISOQUINOLINE-4,4'-PIPERIDINE COMPOUNDS HAVING MULTIMODAL ACTIVITY AGAINST PAIN

(71) Applicant: ESTEVE PHARMACEUTICALS, S.A., Barcelona (ES)

(72) Inventor: Carmen Almansa-Rosales, Barcelona (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 15/571,352

(22) PCT Filed: May 4, 2016

(86) PCT No.: PCT/EP2016/000740
§ 371 (c)(1),
(2) Date: Nov. 2, 2017

(87) PCT Pub. No.: WO2016/177472
PCT Pub. Date: Nov. 10, 2016

(65) Prior Publication Data
US 2018/0230148 A1     Aug. 16, 2018

(30) Foreign Application Priority Data
May 5, 2015  (EP) .................................... 15382232

(51) Int. Cl.
*C07D 471/10* (2006.01)
(52) U.S. Cl.
CPC ................. *C07D 471/10* (2013.01)

(58) Field of Classification Search
CPC .................................................. C07D 471/10
See application file for complete search history.

(56) References Cited

FOREIGN PATENT DOCUMENTS

| CN | 1535967 | | 10/2004 | |
|---|---|---|---|---|
| EP | 1790639 | * | 3/2014 | ........... C07D 233/64 |
| WO | WO2005/063745 A2 | | 7/2005 | |
| WO | WO2006/058303 A2 | | 6/2006 | |

OTHER PUBLICATIONS

Bornot et al., J. Med. Chem, 2013, 56, 1197-1210.
Chien, et al., Neuroscience Letters, 1995, 190, pp. 137-139.
Dickenson, et al., Eur J Pain 9, 113-116 (2005).
Goldberg, et al., BMC Public Health. 11, 770 (2011).
Mao, et al., J. Pain 12, 157-166 (2011).
Turk, et al Lancet 377, 2226-2235 (2011).
Zamanillo, et al., Eur. J. Pharmacol, 716, 78-93 (2013).
International Search Report for PCT/EP2016/000740 dated Jul. 28, 2016.

* cited by examiner

*Primary Examiner* — Noble E Jarrell
(74) *Attorney, Agent, or Firm* — Hueschen and Sage

(57) ABSTRACT

The present invention relates to compounds having dual pharmacological activity towards both the sigma (σ) receptor, and the μ-opiod receptor and more particularly to spiro-isoquinoline-4,4'-piperidine compounds having this pharmacological activity, to processes of preparation of such compounds, to pharmaceutical compositions comprising them, and to their use in therapy, in particular for the treatment of pain.

21 Claims, No Drawings

SPIRO-ISOQUINOLINE-4,4'-PIPERIDINE COMPOUNDS HAVING MULTIMODAL ACTIVITY AGAINST PAIN

FIELD OF THE INVENTION

The present invention relates to compounds having dual pharmacological activity towards both the sigma (σ) receptor, and the μ-opiod receptor (MOR or mu-opioid receptor) and more particularly to spiro-isoquinoline-4,4'-piperidine derivatives having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. Lancet 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. BMC Public Health. 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. Opioids in neuropathic pain: Clues from animal studies. Eur J Pain 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the $\sigma_1$ receptor to analgesia was established by Chien and Pasternak [Chien C C, Pasternak G W. Sigma antagonists potentiate opioid analgesia in rats. Neurosci. Lett. 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma 1 receptor: A new therapeutic target for pain. Eur. J. Pharmacol, 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1 RA, into clinical trials for the treatment of different pain states. Compound S1 RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. J. Pain 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

The authors of the present invention, have found a series of compounds that show dual pharmacological activity towards both the sigma (σ) receptor, and the μ-opioid receptor (MOR or mu-opioid receptor) resulting in an innovative, effective and alternative solution for the treatment of pain.

In view of the existing results of the currently available therapies and clinical practices, the present invention offers a solution by combining in a single compound binding to two different receptors relevant for the treatment of pain. This was mainly achieved by providing the compounds according to the invention that bind both to the μ-opiod receptor and to the $\sigma_1$ receptor.

SUMMARY OF THE INVENTION

In this invention a family of structurally distinct spiro-isoquinoline-4,4'-piperidine derivatives which have a dual pharmacological activity towards both the sigma (σ) receptor, and the μ-opiod receptor was identified thus solving the above problem of identifying alternative or improved pain treatments by offering such dual compounds.

The invention is in one aspect directed to a compound having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a very preferred embodiment if the compound has a binding expressed as $K_i$ which is preferably <1000 nM for both receptors, more preferably <500 nM, even more preferably <100 nM.

The invention is directed in a main aspect to a compound of general Formula (I),

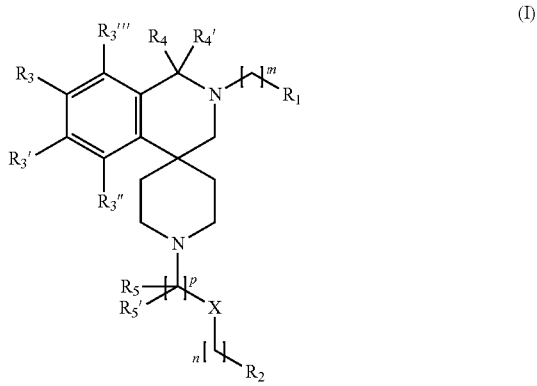

wherein $R_1$, $R_2$, $R_3$, $R_{3'}$, $R_{3''}$, $R_{3'''}$, $R_4$, $R_{4'}$, $R_5$, $R_{5'}$, X, m, n and p are as defined below in the detailed description.

A further object of the invention refers to the processes for preparation of compounds of general formula (I).

A still further object of the invention refers to the use of intermediate compounds for the preparation of a compound of general formula (I).

It is also an object of the invention a pharmaceutical composition comprising a compound of formula (I).

Finally, it is an object of the invention the use of compound as a medicament and more particularly for the treatment of pain and pain related conditions.

DETAILED DESCRIPTION OF THE INVENTION

The invention is directed to a family of structurally distinct spiro-isoquinoline-4,4'-piperidine derivatives which have a dual pharmacological activity towards both the sigma (σ) receptor and the μ-opiod receptor, thus solving the above problem of identifying alternative or improved pain treatments by offering such dual compounds.

The invention is in one aspect directed to a compound having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a preferred embodiment if the compound has a binding expressed as $K_i$ which is preferably <1000 nM for both receptors, more preferably <500 nM, even more preferably <100 nM.

The applicant has surprisingly found that the problem on which the present invention is based can be solved by using a multimodal balanced analgesic approach combining two different synergistic activities in a single drug (i.e., dual ligands which are bifunctional and bind to μ-opioid receptor and to $\sigma_1$ receptor), thereby enhancing the opioid analgesia through the $\sigma_1$ activation without increasing the undesirable side effects. This supports the therapeutic value of a dual MOR/$\sigma_1$ receptor compound whereby the $\sigma_1$ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of μ-opioid receptor agonists.

A dual compound that possess binding to both the μ-opiod receptor and to the $\sigma_1$ receptor shows a highly valuable therapeutic potential by achieving an outstanding analgesia (enhanced in respect to the potency of the opioid component alone) with a reduced side-effect profile (safety margin increased compared to that of the opioid component alone) versus existing opioid therapies.

Advantageously, the dual compounds according to the present invention would in addition show one or more the following functionalities: $\sigma_1$ receptor antagonism and μ-opioid receptor agonism. It has to be noted, though, that both functionalities "antagonism" and "agonism" are also subdivided in their effect into subfunctionalities like partial agonism or inverse agonism. Accordingly, the functionalities of the dual compound should be considered within a relatively broad bandwidth.

An antagonist on one of the named receptors blocks or dampens agonist-mediated responses. Known subfunctionalities are neutral antagonists or inverse agonists.

An agonist on one of the named receptors increases the activity of the receptor above its basal level. Known subfunctionalities are full agonists, or partial agonists.

In addition, the two mechanisms complement each other since MOR agonists are only marginally effective in the treatment of neuropathic pain, while $\sigma_1$ receptor antagonists show outstanding effects in preclinical neuropathic pain models. Thus, the $\sigma_1$ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. *J. Med. Chem*, 56, 1197-1210 (2013)].

In a particular aspect, the present invention is directed to compounds of general Formula (I):

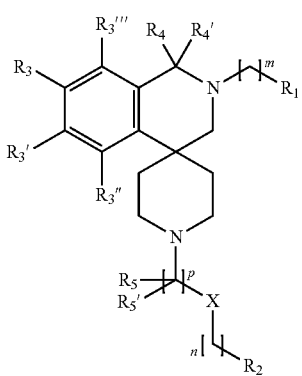

(I)

wherein
- m is 0, 1, 2, 3, 4, 5 or 6;
- n is 0, 1, 2, 3 or 4;
- p is 1, 2 or 3;
- $R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —C(O)$R_6$, —C(O)O$R_6$, —C(O)N$R_6R_6$, and —S(O)$_2R_6$;
  - wherein wherein $R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
- $R_2$ is selected from substituted or unsubstituted monocyclic $C_{3-7}$ cycloalkyl, substituted or unsubstituted monocyclic aryl and substituted or unsubstituted monocyclic heterocyclyl;
- X is selected from a bond, —C($R_xR_{x'}$)—, and —C($R_x$)(O$R_7$)—;
  - $R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)O$R_7$, —C(O)N$R_7R_{7'}$, —N$R_7$C(O)$R_{7'}$, and N$R_7R_{7''}$;
  - $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
  - $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;
  - and wherein $R_{7'''}$ is selected from hydrogen, unsubstituted $C_{1-6}$ alkyl, unsubstituted $C_{2-6}$ alkenyl, unsubstituted $C_{2-6}$ alkynyl and -Boc;
- $R_3$ is selected from hydrogen, halogen, —$R_9$, —O$R_9$, —NO$_2$, —N$R_9R_{9'''}$, —N$R_9$C(O)$R_{9'}$, —NC(O)O$R_9$, —N$R_9$S(O)$_2R_{9'}$, —S(O)$_2$N$R_9R_{9'}$, —N$R_9$C(O)N$R_9R_{9''}$, —S$R_9$, —S(O)R_9, —S(O)_2R_9, —CN, haloalkyl, haloalkoxy, —C(O)O$R_9$, —C(O)N$R_9R_{9'}$, —N$R_9$S(O)$_2$N$R_9R_{9''}$, and —OC(O)$R_9$;
- $R_{3'}$, $R_{3''}$ and $R_{3'''}$ are independently selected from hydrogen, halogen, —$R_9$, —O$R_9$, —NO$_2$, —N$R_9R_{9'''}$, —N$R_9$C(O)$R_{9'}$, —NC(O)O$R_9$, —N$R_9$S(O)$_2R_{9'}$, —S(O)$_2$N$R_9R_{9'}$, —N$R_9$C(O)N$R_9R_{9''}$, —S$R_9$, —S(O)R_9, —S(O)_2R_9, —CN, haloalkyl, haloalkoxy, —C(O)O$R_9$, —C(O)N$R_9R_{9'}$, —N$R_9$S(O)$_2$N$R_9R_{9''}$ and —OC(O)$R_9$;
  - wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;
  - and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;
- $R_4$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)O$R_8$, —C(O)N$R_8R_{8'}$;
- $R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;
  - wherein $R_8$, $R_{8'}$ and $R_{8''}$ are independently selected from hydrogen, unsubstituted $C_{1-6}$ alkyl, unsubstituted $C_{2-6}$ alkenyl, and unsubstituted $C_{2-6}$ alkynyl;
  - and wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc;
- alternatively, $R_4$ and $R_{4'}$ may form together with the carbon to which they are attached, a C=O group;
- $R_5$ and $R_{5'}$ are independently selected from hydrogen, or substituted or unsubstituted $C_{1-6}$ alkyl, substituted or unsubstituted $C_{2-6}$ alkenyl, and substituted or unsubstituted $C_{2-6}$ alkynyl;

These compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a particular embodiment the following proviso applies:
when —[CH$_2$]$_m$—$R_1$ is —C(O)$R_6$, —C(O)O$R_6$, —C(O)N$R_6R_{6'}$ or —S(O)$_2R_6$,
then —X—[CH$_2$]$_n$—$R_2$ is not substituted or unsubstituted aryl, substituted or unsubstituted heterocyclyl or substituted or unsubstituted cycloalkyl.

In another particular embodiment the following proviso applies:
when —[CH$_2$]$_m$—$R_1$ is —C(O)$R_6$, —C(O)O$R_6$, —C(O)N$R_6R_{6'}$ or —S(O)$_2R_6$,
and $R_4$ and $R_{4'}$ are both hydrogen,
then —X—[CH$_2$]$_n$—$R_2$ is not substituted or unsubstituted aryl, substituted or unsubstituted heterocyclyl or substituted or unsubstituted cycloalkyl.

In another particular embodiment the following proviso applies:
when —[CH$_2$]$_m$—$R_1$ is —C(O)$R_6$, —C(O)O$R_6$, —C(O)N$R_6R_{6'}$ or —S(O)$_2R_6$,
then —[C$R_5R_{5'}$]$_p$—X—[CH$_2$]$_n$ is not —CH$_2$—.

In another particular embodiment the following proviso applies:
when —[CH$_2$]$_m$—$R_1$ is —C(O)$R_6$, —C(O)O$R_6$, —C(O)N$R_6R_{6'}$ or —S(O)$_2R_6$,
and $R_4$ and $R_{4'}$ are both hydrogen,
then —[C$R_5R_{5'}$]$_p$—X—[CH$_2$]$_n$ is not —CH$_2$—.

In another particular embodiment the following proviso applies:

when $R_4$ and $R_{4'}$ are both hydrogen, then —$[CH_2]_m$—$R_1$ is not H,

In another particular embodiment the following proviso applies:

when any of $R_3$, $R_{3'}$, $R_{3''}$ and $R_{3'''}$ is not hydrogen, and $R_4$ and $R_{4'}$ are both hydrogen, and —$[CH_2]_m$—$R_1$ is H, then —$[CR_5R_{5'}]_q$—X—$[CH_2]_n$—$R_2$ is not benzyl.

In another particular embodiment the following proviso applies:

when $R_4$ and $R_{4'}$ are both hydrogen, then —$[CR_5R_{5'}]_p$—X—$[CH_2]_n$—$R_2$ is not benzyl.

In a particular embodiment the following compound is excluded:

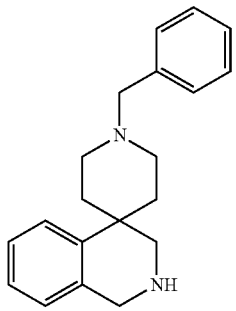 [SMILES: c1ccc(CN2CCC3(CC2)CNCc2ccccc23)cc1]

In a further embodiment the compound according to the invention of general Formula (I) is a compound of general Formula (I')

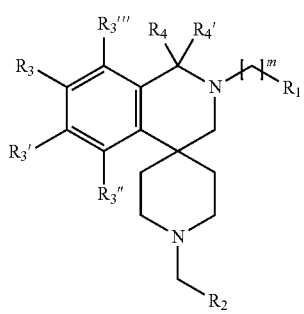

(I')

wherein $R_1$, $R_2$, $R_3$, $R_{3'}$, $R_{3''}$, $R_{3'''}$, $R_4$, $R_{4'}$, $R_5$, $R_{5'}$ and m are as defined in the description.

In a further embodiment the compound according to the invention of general Formula (I) is a compound of general Formula (I$^{2'}$)

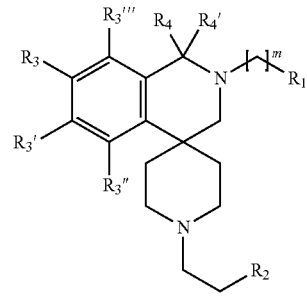

(I$^{2'}$)

wherein $R_1$, $R_2$, $R_3$, $R_{3'}$, $R_{3''}$, $R_{3'''}$, $R_4$, $R_{4'}$, $R_5$, $R_{5'}$ and m are as defined in the description.

In a further embodiment the compound according to the invention of general Formula (I) is a compound of general Formula (I$^{3'}$)

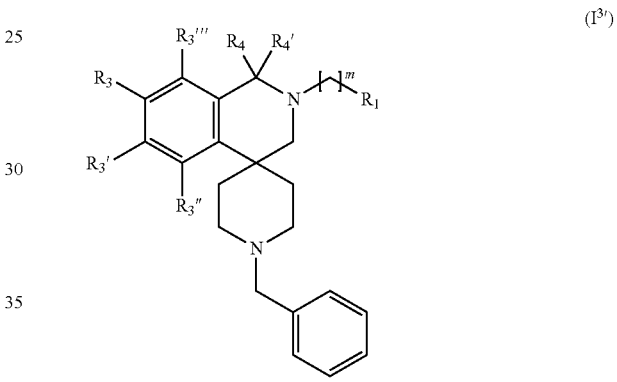

(I$^{3'}$)

wherein $R_1$, $R_3$, $R_{3'}$, $R_{3''}$, $R_{3'''}$, $R_4$, $R_{4'}$, $R_5$, $R_{5'}$ and m are as defined in the description.

In a further embodiment the compound according to the invention of general Formula (I) is a compound of general Formula (I$^{4'}$)

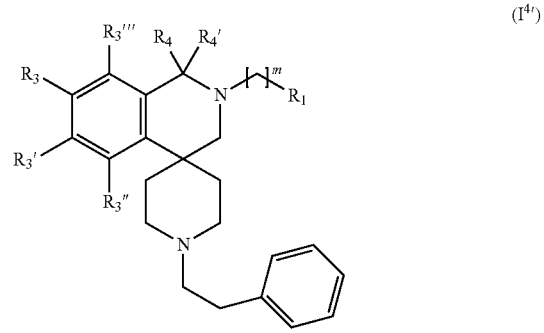

(I$^{4'}$)

wherein $R_1$, $R_3$, $R_{3'}$, $R_{3''}$, $R_{3'''}$, $R_4$, $R_{4'}$, $R_5$, $R_{5'}$ and m are as defined in the description.

In a further embodiment the compound according to the invention of general Formula (I) is a compound of general Formula (I$^{5'}$)

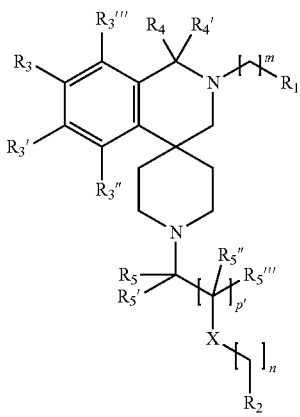

wherein $R_1$, $R_2$, $R_3$, $R_3'$, $R_3''$, $R_3'''$, $R_4$, $R_4'$, $R_5$, $R_5'$, m, n and X are as defined in the description. In addition, p', $R_5''$ and $R_5'''$ are added. These are reflecting the statements below in the definitions of substitutions on alkyl etc. or aryl etc. that "when different radicals $R_1$ to $R_{13}$ and $R_x$ are present simultaneously in Formula I they may be identical or different". Thus this is reflecting that $R_5''$ and $R_5'''$ are or could be different from $R_5$ and $R_5'$ or not and—accordingly—p' being 0 or 1 or 2 is naturally resulting from p being 1, 2 or 3.

For clarity purposes, all groups and definitions described in the present description and referring to compounds of general Formula (I), also apply to compounds of general Formula (I'), (I$^{2'}$), (I$^{3'}$) or (I$^{4'}$) or (I$^{5'}$) (where applicable), since compounds of general Formula (I'), (I$^{2'}$), (I$^{3'}$) or (I$^{4'}$) or (I$^{5'}$) are included within the scope of the larger definition of general Formula (I).

For clarity purposes, the general Markush Formula (I)

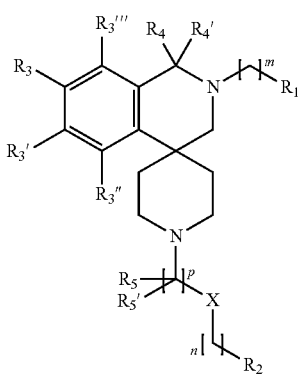

is equivalent to

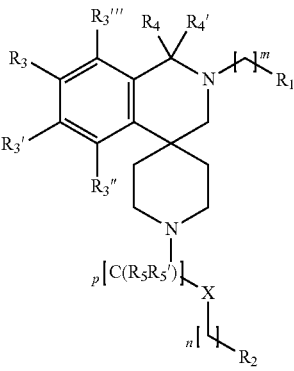

wherein only —C($R_5R_5'$)— are included into the brackets and p means the number of times that —C($R_5R_5'$)— is repeated. The same would apply to general Markush Formulae (I'), (I$^{2'}$), (I$^{3'}$), (I$^{4'}$) or (I$^{5'}$)

In addition, and for clarity purposes, it should further be understood that naturally if n is 0, $R_2$ is still present in general Markush Formulae (I), (I'), (I$^{2'}$), (I$^{3'}$), (I$^{4'}$) or (I$^{5'}$).

In the context of this invention, alkyl is understood as meaning saturated, linear or branched hydrocarbons, which may be unsubstituted or substituted once or several times. It encompasses e.g. —CH$_3$ and —CH$_2$—CH$_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also CHF$_2$, CF$_3$ or CH$_2$OH etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH═CH—CH$_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—CH$_3$ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by halogen (F, Cl, Br, I), —NR$_c$R$_{c'''}$, —SR$_c$, —S(O)R$_c$, —S(O)$_2$R$_c$, —OR$_c$, —C(O)OR$_c$, —CN, —C(O)NR$_c$R$_{c'}$, haloalkyl, haloalkoxy or —OC$_{1-4}$alkyl, being R$_c$ represented by R$_{11}$, R$_{12}$, R$_{10}$, (being R$_{c'}$ represented by R$_{11}'$, R$_{12}'$, R$_{10}'$; being R$_{c''}$ represented by R$_{11}''$, R$_{12}''$, R$_{10}''$; being R$_{c'''}$ represented by R$_{11}'''$, R$_{12}'''$, R$_{10}'''$, being R$_{c''''}$ represented by R$_{11}''''$, R$_{12}''''$, R$_{10}''''$) wherein R$_1$ to R$_{13}''''$ and R$_x$ are as defined in the description, and wherein when different radicals R$_1$ to R$_{13}''''$ and R$_x$ are present simultaneously in Formula I they may be identical or different.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which is substituted is substituted with one or more of halogen (F, Cl, Br, I), —OR$_c$, —CN, —SR$_c$, —S(O)R$_c$, and —S(O)$_2$R$_c$, haloalkyl, haloalkoxy or —OC$_{1-4}$alkyl, being R$_c$ represented by R$_{11}$, R$_{12}$, R$_{10}$, (being R$_{c'}$ represented by R$_{11}'$, R$_{12}'$, R$_{10}'$; being R$_{c''}$ represented by R$_{11}''$, R$_{12}''$, R$_{10}''$; being R$_{c'''}$ represented by R$_{11}'''$, R$_{12}'''$, R$_{10}'''$, being R$_{c''''}$ represented by R$_{11}''''$, R$_{12}''''$, R$_{10}''''$), wherein R$_1$ to R$_{1}''''$ and R$_x$ are as defined in the description, and wherein when different radicals R$_1$ to R$_{13}''''$ and R$_x$ are present simultaneously in Formula I they may be identical or different.

More than one replacement on the same molecule and also on the same carbon atom is possible with the same or different substituents. This includes for example 3 hydrogens being replaced on the same C atom, as in the case of CF$_3$, or at different places of the same molecule, as in the case of e.g. —CH(OH)—CH=CH—CHCl$_2$.

In the context of this invention haloalkyl is understood as meaning an alkyl being substituted once or several times by a halogen (selected from F, Cl, Br, I). It encompasses e.g. —CH$_2$Cl, —CH$_2$F, —CHCl$_2$, —CHF$_2$, —CCl$_3$, —CF$_3$ and —CH$_2$—CHCl$_2$. Preferably haloalkyl is understood in the context of this invention as halogen-substituted C$_{1-4}$-alkyl representing halogen substituted C1-, C2-, C3- or C4-alkyl. The halogen-substituted alkyl radicals are thus preferably methyl, ethyl, propyl, and butyl. Preferred examples include —CH$_2$Cl, —CH$_2$F, —CHCl$_2$, —CHF$_2$, and —CF$_3$.

In the context of this invention haloalkoxy is understood as meaning an —O-alkyl being substituted once or several times by a halogen (selected from F, Cl, Br, I). It encompasses e.g. —OCH$_2$Cl, —OCH$_2$F, —OCHCl$_2$, —OCHF$_2$, —OCCl$_3$, —OCF$_3$ and —OCH$_2$—CHCl$_2$. Preferably haloalkyl is understood in the context of this invention as halogen-substituted —OC$_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —OCH$_2$Cl, —OCH$_2$F, —OCHCl$_2$, —OCHF$_2$, and —OCF$_3$.

In the context of this invention cycloalkyl is understood as meaning saturated and unsaturated (but not aromatic) cyclic hydrocarbons (without a heteroatom in the ring), which can be unsubstituted or once or several times substituted. Furthermore, C$_{3-4}$-cycloalkyl represents C3- or C4-cycloalkyl, C$_{3-5}$-cycloalkyl represents C3-, C4- or C5-cycloalkyl, C$_{3-6}$-cycloalkyl represents C3-, C4-, C5- or C6-cycloalkyl, C$_{3-7}$-cycloalkyl represents C3-, C4-, C5-, C6- or C7-cycloalkyl, C$_{3-8}$-cycloalkyl represents C3-, C4-, C5-, C6-, C7- or C8-cycloalkyl, C$_{4-5}$-cycloalkyl represents C4- or C5-cycloalkyl, C$_{4-6}$-cycloalkyl represents C4-, C5- or C6-cycloalkyl, C$_{4-7}$-cycloalkyl represents C4-, C5-, C6- or C7-cycloalkyl, C$_{5-6}$-cycloalkyl represents C5- or C6-cycloalkyl and C$_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is C$_{3-8}$cycloalkyl like cyclopropyl, cyclobutyl, cyclopentyl, cyclohexyl, cycloheptyl, or cyclooctyl; or is C$_{3-7}$cycloalkyl like cyclopropyl, cyclobutyl, cyclopentyl, cyclohexyl, or cycloheptyl; or is C$_{3-6}$cycloalkyl like cyclopropyl, cyclobutyl, cyclopentyl or cyclohexyl, especially cyclopentyl or cyclohexyl.

Aryl is understood as meaning 5 to 18 membered mono or polycyclic ring systems with at least one aromatic ring but without heteroatoms even in only one of the rings. Examples are phenyl, naphthyl, fluoranthenyl, fluorenyl, tetralinyl, indanyl, 9H-fluorenyl or anthracenyl radicals, which can be unsubstituted or once or several times substituted. Most preferably aryl is understood in the context of this invention as phenyl, naphtyl or anthracenyl, preferably is phenyl.

A heterocyclyl radical or group (also called heterocyclyl hereinafter) is understood as meaning 5 to 18 membered mono or polycyclic heterocyclic ring systems, with at least one saturated or unsaturated ring which contains one or more heteroatoms from the group consisting of nitrogen, oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.

the heteroaryl (being equivalent to heteroaromatic radicals or aromatic heterocyclyls) is an aromatic 5 to 18 membered heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic heterocyclyl is a 5 to 18 membered heterocyclic ring system of one or more rings of which at least one ring—with this (or these) ring(s) then not being aromatic—contains one or more heteroatoms from the group consisting of nitrogen, oxygen and/or sulfur in the ring; preferably is a heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, especially is benzodioxane, morpholine, tetrahydropyran, piperidine, oxopyrrolidine and pyrrolidine.

Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring.

Preferred examples of heterocyclyls include oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b]pyridine, benzoxazole, oxopyrrolidine, pyrimidine, oxazepane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning an heterocyclyl group being connected to another atom through a $C_{1-6}$-alkyl (see above) which may be branched or linear and is unsubstituted or substituted once or several times. Preferably alkylheterocyclyl is understood as meaning an heterocyclyl group (see above) being connected to another atom through 1 to 4 (—$CH_2$—) groups. Most preferably alkylheterocyclyl is —$CH_2$-pyridine.

In the context of this invention alkylcycloalkyl is understood as meaning an cycloalkyl group being connected to another atom through a $C_{1-6}$-alkyl (see above) which may be branched or linear and is unsubstituted or substituted once or several times. Preferably alkylcycloalkyl is understood as meaning an cycloalkyl group (see above) being connected to another atom through 1 to 4 (—$CH_2$—) groups. Most preferably alkylcycloalkyl is —$CH_2$-cyclopropyl.

Preferably, the aryl is a monocyclic aryl. More preferably the aryl is a 5, 6 or 7 membered monocyclic aryl. Even more preferably the aryl is a 5 or 6 membered monocyclic aryl.

Preferably, the heteroaryl is a monocyclic heteroaryl. More preferably the heteroaryl is a 5, 6 or 7 membered monocyclic heteroaryl. Even more preferably the heteroaryl is a 5 or 6 membered monocyclic heteroaryl.

Preferably, the non-aromatic heterocyclyl is a monocyclic non-aromatic heterocyclyl. More preferably the non-aromatic heterocyclyl is a 4, 5, 6 or 7 membered monocyclic non-aromatic heterocyclyl. Even more preferably the non-aromatic heterocyclyl is a 5 or 6 membered monocyclic non-aromatic heterocyclyl.

Preferably, the cycloalkyl is a monocyclic cycloalkyl. More preferably the cycloalkyl is a 3, 4, 5, 6, 7 or 8 membered monocyclic cycloalkyl. Even more preferably the cycloalkyl is a 3, 4, 5 or 6 membered monocyclic cycloalkyl.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl with one or more of halogen (F, Cl, Br, I), —$R_c$, —CN, —$NO_2$, —$NR_cR_{c'''}$, —C(O)$OR_c$, $NR_cC(O)R_{c'}$, —C(O)$NR_cR_{c'}$, —$NR_cS(O)_2R_{c'}$, =O, —$OCH_2CH_2OH$, —$NR_cC(O)NR_{c'}R_{c''}$, —S(O)$_2NR_cR_{c'}$, —$NR_cS(O)_2NR_{c'}R_{c''}$, haloalkyl, haloalkoxy, —$SR_c$, —S(O)$R_c$, —S(O)$_2R_c$ or C($CH_3$)$OR_c$; $NR_cR_{c'''}$, with $R_c$, $R_{c'}$, $R_{c''}$ and $R_{c'''}$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_c$ one of $R_{11}$, $R_{12}$ or $R_{13}$, (being $R_{c'}$, one of $R_{11'}$, $R_{12'}$ or $R_{13'}$; being $R_{c''}$ one of $R_{11''}$, $R_{12''}$ or $R_{13''}$; being $R_{c'''}$ one of $R_{11'''}$, $R_{12'''}$ or $R_{13'''}$; being $R_{c''''}$ one of $R_{11''''}$, $R_{12''''}$ or $R_{13''''}$), wherein $R_1$ to $R_{13''''}$ and $R_x$ are as defined in the description, and wherein when different radicals $R_1$ to $R_{13''''}$ and $R_x$ are present simultaneously in Formula I they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted (also in an alyklaryl, alkylcycloalkyl or alkylheterocyclyl) with one or more of halogen (F, Cl, Br, I), —$R_c$, —$OR_c$, —CN, —$NO_2$, —$NR_cR_{c'}$—, $NR_cC(O)R_{c'}$, —$NR_cS(O)_2R_{c'}$, =O, haloalkyl, haloalkoxy, or C($CH_3$)$OR_c$; —$OC_{1-4}$alkyl being unsubstituted or substituted with one or more of $OR_c$ or halogen (F, Cl, I, Br), —CN, or —$C_{1-4}$alkyl being unsubstituted or substituted with one or more of $OR_c$ or halogen (F, Cl, I, Br), being $R_c$ one of $R_{11}$, $R_{12}$ or $R_{13}$, (being $R_{c'}$ one of $R_{11'}$, $R_{12'}$ or $R_{13'}$; being $R_{c''}$ one of $R_{11''}$, $R_{12''}$ or $R_{13''}$; being $R_{c'''}$ one of $R_{11'''}$, $R_{12'''}$ or $R_{13'''}$; being $R_{c''''}$ one of $R_{11''''}$, $R_{12''''}$ or $R_{13''''}$), wherein $R_1$ to $R_{13''''}$ and $R_x$ are as defined in the description, and wherein when different radicals $R_1$ to $R_{13''''}$ and $R_x$ are present simultaneously in Formula I they may be identical or different.

In connection with cycloalkyl (including alkyl-cycloalkyl), or heterocycly (including alkylheterocyclyl)

namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with

(leading to a spiro structure) or =O.

A ring system is a system consisting of at least one ring of connected atoms but including also systems in which two or more rings of connected atoms are joined with "joined" meaning that the respective rings are sharing one (like a spiro structure), two or more atoms being a member or members of both joined rings.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic—especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or of a nitrogen by $^{15}N$-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general Formula (I) is a compound wherein
m is 0, 1, 2, 3, 4, 5 or 6;
n is 0, 1, 2, 3 or 4;
p is 1, 2 or 3;
$R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —$C(O)R_6$, —$C(O)OR_6$, —$C(O)NR_6R_{6'}$ and —$S(O)_2R_6$;
  wherein $R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
  wherein said cycloalkyl, aryl or heterocyclyl in $R_1$, if substituted, is substituted with one or more substituent/s selected from halogen, —$R_{11}$, —$OR_{11}$, —$NO_2$, —$NR_{11}R_{11'''}$,  $NR_{11}C(O)R_{11'}$,  —$NR_{11}S(O)_2R_{11'}$, —S(O)$_2$NR$_{11}$R$_{11'}$, —NR$_{11}$C(O)NR$_{11'}$R$_{11''}$, —SR$_{11}$, —S(O)R$_{11}$, S(O)$_2$R$_{11}$, —CN, haloalkyl, haloalkoxy, —C(O)OR$_{11}$, —C(O)NR$_{11}$R$_{11'}$, and NR$_{11}$S(O)$_2$NR$_{11'}$R$_{11''}$;

wherein said cycloalkyl or non-aromatic heterocyclyl in R$_1$, if substituted, may also be substituted with

or =O;

wherein the alkyl, alkenyl or alkynyl in R$_1$ or R$_6$, if substituted, is substituted with one or more substituent/s selected from —OR$_{11}$, halogen, —CN, haloalkyl, haloalkoxy, —SR$_{11}$, —S(O)R$_{11}$, and —S(O)$_2$R$_{11}$;

wherein R$_{11}$, R$_{11'}$, and R$_{11''}$, are independently selected from hydrogen, unsubstituted C$_{1-6}$ alkyl, unsubstituted C$_{2-6}$ alkenyl, unsubstituted C$_{2-6}$ alkynyl;

and wherein R$_{11'''}$ is selected from hydrogen, unsubstituted C$_{1-6}$ alkyl, unsubstituted C$_{2-6}$ alkenyl, unsubstituted C$_{2-6}$ alkynyl and -Boc;

R$_2$ is selected from substituted or unsubstituted monocyclic C$_{3-7}$ cycloalkyl, substituted or unsubstituted monocyclic aryl and substituted or unsubstituted monocyclic heterocyclyl;

wherein said cycloalkyl, aryl or heterocyclyl in R$_2$, if substituted, is substituted with one or more substituent/s selected from halogen, —R$_{12}$, —OR$_{12}$, —NO$_2$, —NR$_{12}$R$_{12'''}$, NR$_{12}$C(O)R$_{12'}$, —NR$_{12}$S(O)$_2$R$_{12'}$, —S(O)$_2$NR$_{12}$R$_{12'}$, —NR$_{12}$C(O)NR$_{12'}$R$_{12''}$, —SR$_{12}$, —S(O)R$_{12}$, S(O)$_2$R$_{12}$, —CN, haloalkyl, haloalkoxy, —C(O)OR$_{12}$, —C(O)NR$_{12}$R$_{12'}$, and NR$_{12}$S(O)$_2$NR$_{12'}$R$_{12''}$;

wherein said cycloalkyl or non-aromatic heterocyclyl in R$_2$, if substituted, may also be substituted with

or =O;

wherein R$_{12}$, R$_{12'}$ and R$_{12''}$ are independently selected from hydrogen, unsubstituted C$_{1-6}$ alkyl, and unsubstituted C$_{2-6}$ alkenyl, unsubstituted C$_{2-6}$ alkynyl;

and wherein R$_{12'''}$ is selected from hydrogen, unsubstituted C$_{1-6}$ alkyl, unsubstituted C$_{2-6}$ alkenyl, unsubstituted C$_{2-6}$ alkynyl and -Boc;

X is selected from a bond, —C(R$_x$R$_{x'}$)—, and —C(R$_x$)(OR$_7$)—;

R$_x$ is selected from hydrogen, substituted or unsubstituted C$_{1-6}$ alkyl, substituted or unsubstituted C$_{2-6}$ alkenyl, substituted or unsubstituted C$_{2-6}$ alkynyl, —C(O)OR$_7$, —C(O)NR$_7$R$_{7'}$, —NR$_7$C(O)R$_{7'}$, and —NR$_7$R$_{7'''}$;

R$_{x'}$ is selected from hydrogen, substituted or unsubstituted C$_{1-6}$ alkyl, substituted or unsubstituted C$_{2-6}$ alkenyl and substituted or unsubstituted C$_{2-6}$ alkynyl;

R$_7$, R$_{7'}$ and R$_{7''}$ are independently selected from hydrogen, unsubstituted C$_{1-6}$ alkyl, unsubstituted C$_{2-6}$ alkenyl, and unsubstituted C$_{2-6}$ alkynyl;

and wherein R$_{7'''}$ is selected from hydrogen, unsubstituted C$_{1-6}$ alkyl, unsubstituted C$_{2-6}$ alkenyl, unsubstituted C$_{2-6}$ alkynyl and -Boc;

R$_3$ is selected from hydrogen, halogen, —R$_9$, —OR$_9$, —NO$_2$, —NR$_9$R$_{9'''}$, —NR$_9$C(O)R$_{9'}$, —NR$_9$S(O)$_2$R$_{9'}$, —S(O)$_2$NR$_9$R$_{9'}$, —NR$_9$C(O)NR$_9$R$_{9''}$, —SR$_9$, —S(O)R$_9$, S(O)$_2$R$_9$, —CN, haloalkyl, haloalkoxy, —C(O)OR$_9$, —C(O)NR$_9$R$_{9'}$, —NR$_9$S(O)$_2$NR$_9$R$_{9''}$, and —OC(O)R$_9$;

R$_{3'}$, R$_{3''}$ and R$_{3'''}$ are independently selected from hydrogen, halogen, —R$_9$, —OR$_9$, —NO$_2$, —NR$_9$R$_{9'''}$, —NR$_9$C(O)R$_{9'}$, —NR$_9$S(O)$_2$R$_{9'}$, —S(O)$_2$NR$_9$R$_{9'}$, —NR$_9$C(O)NR$_9$R$_{9''}$, —SR$_9$, —S(O)R$_9$, S(O)$_2$R$_9$, —CN, haloalkyl, haloalkoxy, —C(O)OR$_9$, —C(O)NR$_9$R$_{9'}$, —NR$_9$S(O)$_2$NR$_9$R$_{9''}$ and —OC(O)R$_9$;

wherein R$_9$, R$_{9'}$ and R$_{9''}$ are independently selected from hydrogen, unsubstituted C$_{1-6}$ alkyl, unsubstituted C$_{2-6}$ alkenyl, and unsubstituted C$_{2-6}$ alkynyl;

and wherein R$_{9'''}$ is selected from hydrogen, unsubstituted C$_{1-6}$ alkyl, unsubstituted C$_{2-6}$ alkenyl, unsubstituted C$_{2-6}$ alkynyl and -Boc;

R$_4$ is selected from hydrogen, substituted or unsubstituted C$_{1-6}$ alkyl, substituted or unsubstituted C$_{2-6}$ alkenyl, substituted or unsubstituted C$_{2-6}$ alkynyl, —C(O)OR$_8$, —C(O)NR$_8$R$_{8'}$;

R$_{4'}$ is selected from hydrogen, or substituted or unsubstituted C$_{1-6}$ alkyl, substituted or unsubstituted C$_{2-6}$ alkenyl, and substituted or unsubstituted C$_{2-6}$ alkynyl;

wherein R$_8$, R$_{8'}$ and R$_{8''}$ are independently selected from hydrogen, unsubstituted C$_{1-6}$ alkyl, unsubstituted C$_{2-6}$ alkenyl, and unsubstituted C$_{2-6}$ alkynyl;

and wherein R$_{8'''}$ is selected from hydrogen, unsubstituted C$_{1-6}$ alkyl, unsubstituted C$_{2-6}$ alkenyl, unsubstituted C$_{2-6}$ alkynyl and -Boc;

alternatively, R$_4$ and R$_{4'}$ may form together with the carbon to which they are attached, a C=O group;

R$_5$ and R$_{5'}$ are independently selected from hydrogen, or substituted or unsubstituted C$_{1-6}$ alkyl, substituted or unsubstituted C$_{2-6}$ alkenyl, and substituted or unsubstituted C$_{2-6}$ alkynyl;

the alkyl, alkenyl or alkynyl, other than those defined in R$_1$, R$_2$ or R$_6$, if substituted, is substituted with one or more substituent/s selected from —OR$_{10}$, halogen, —CN, haloalkyl, haloalkoxy, —SR$_{10}$, —S(O)R$_{10}$, and —S(O)$_2$R$_{10}$;

wherein R$_{10}$, and R$_{10'}$ are independently selected from hydrogen, unsubstituted C$_{1-6}$ alkyl, unsubstituted C$_{2-6}$ alkenyl, and unsubstituted C$_{2-6}$ alkynyl;

the aryl, heterocyclyl or cycloalkyl, other than those defined in R$_1$, R$_2$ or R$_6$, if substituted, is substituted with one or more substituent/s selected from halogen, —R$_{13}$, —OR$_{13}$, —NO$_2$, —NR$_{13}$R$_{13'''}$, NR$_{13}$C(O)R$_{13'}$, —NR$_{13}$S(O)$_2$R$_{13'}$, —S(O)$_2$NR$_{13}$R$_{13'}$, —NR$_{13}$C(O)NR$_{13'}$R$_{13''}$, —SR$_{13}$, —S(O)R$_{13}$, S(O)$_2$R$_{13}$, —CN, haloalkyl, haloalkoxy, —C(O)OR$_{13}$, —C(O)NR$_{13}$R$_{13'}$, and —NR$_{13}$S(O)$_2$NR$_{13'}$R$_{13''}$;

wherein said cycloalkyl or non-aromatic heterocyclyl, other than those defined in R$_1$, R$_2$ or R$_6$, if substituted, may also be substituted with

or =O;

wherein R$_{13}$, R$_{13'}$ and R$_{13''}$ are independently selected from hydrogen, unsubstituted C$_{1-6}$ alkyl, unsubstituted C$_{2-6}$ alkenyl, unsubstituted C$_{2-6}$ alkynyl, unsubstituted aryl, unsubstituted cycloalkyl and unsubstituted heterocyclyl;

and wherein R$_{13'''}$ is selected from hydrogen, unsubstituted C$_{1-6}$ alkyl, unsubstituted C$_{2-6}$ alkenyl, unsubstituted C$_{2-6}$ alkynyl and -Boc;

These preferred compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein m is 0, 1, 2, 3, 4, 5 or 6;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein n is 0, 1, 2, 3 or 4;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein p is 1, 2 or 3;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein X is selected from a bond, $-C(R_xR_{x'})-$, and $-C(R_x)(OR_7)-$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, $-C(O)R_6$, $-C(O)OR_6$, $-C(O)NR_6R_{6'}$ and $-S(O)_2R_6$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from substituted or unsubstituted $C_{1-6}$ alkyl, substituted or unsubstituted $C_{2-6}$ alkenyl, substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is substituted or unsubstituted cycloalkyl, substituted or unsubstituted aryl, substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is $-C(O)R_6$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is $-C(O)OR_6$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is $-C(O)NR_6R_{6'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is $-S(O)_2R_6$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from substituted or unsubstituted monocyclic $C_{3-7}$ cycloalkyl, substituted or unsubstituted monocyclic aryl and substituted or unsubstituted monocyclic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is substituted or unsubstituted monocyclic aryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_3$ is selected from hydrogen, halogen, —$R_9$, —$OR_9$, —$NO_2$, —$NR_9R_{9'''}$, —$NR_9C(O)R_{9'}$, —$NR_9S(O)_2R_{9'}$, —$S(O)_2NR_9R_{9'}$, —$NR_9C(O)NR_9R_{9''}$, —$SR_9$, —$S(O)R_9$, $S(O)_2R_9$, —CN, haloalkyl, haloalkoxy, —$C(O)OR_9$, —$C(O)NR_9R_{9'}$, —$NR_9S(O)_2NR_9R_{9''}$ and —$OC(O)R_9$;

$R_{3'}$, $R_{3''}$ and $R_{3'''}$ are independently selected from hydrogen, halogen, —$R_9$, —$OR_9$, —$NO_2$, —$NR_9R_{9'''}$, —$NR_9C(O)R_{9'}$, —$NR_9S(O)_2R_{9'}$, —$S(O)_2NR_9R_{9'}$, —$NR_9C(O)NR_9R_{9'''}$, —$SR_9$, —$S(O)R_9$, $S(O)_2R_9$, —CN, haloalkyl, haloalkoxy, —$C(O)OR_9$, —$C(O)NR_9R_{9'}$, —$NR_9S(O)_2NR_9R_{9''}$ and —$OC(O)R_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_3$ is selected from hydrogen, halogen, —$R_9$, —$OR_9$, —$NO_2$, —$NR_9R_{9'''}$, —$NR_9C(O)R_{9'}$, —$NR_9S(O)_2R_{9'}$, —$S(O)_2NR_9R_{9'}$, —$NR_9C(O)NR_9R_{9''}$, —$SR_9$, —$S(O)R_9$, $S(O)_2R_9$, —CN, haloalkyl, haloalkoxy, —$C(O)OR_9$, —$C(O)NR_9R_{9'}$, —$NR_9S(O)_2NR_9R_{9''}$ and —$OC(O)R_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_{3'}$, $R_{3''}$ and $R_{3'''}$ are independently selected from hydrogen, halogen, —$R_9$, —$OR_9$, —$NO_2$, —$NR_9R_{9'''}$, —$NR_9C(O)R_{9'}$, —$NR_9S(O)_2R_{9'}$, —$S(O)_2NR_9R_{9'}$, —$NR_9C(O)NR_9R_{9'''}$, —$SR_9$, —$S(O)R_9$, $S(O)_2R_9$, —CN, haloalkyl, haloalkoxy, —$C(O)OR_9$, —$C(O)NR_9R_{9'}$, —$NR_9S(O)_2NR_9R_{9''}$ and —$OC(O)R_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ is selected from hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —$C(O)OR_8$, —$C(O)NR_8R_{8'}$, —$NR_8C(O)R_{8'}$, —$NR_8R_{8'''}$ and —$NR_8C(O)OR_{8'}$;

$R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —$C(O)OR_8$, —$C(O)NR_8R_{8'}$;

$R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ is selected from hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —$C(O)OR_8$, —$C(O)NR_8R_{8'}$, —$NR_8C(O)R_{8'}$, —$NR_8R_{8'''}$ and $NR_8C(O)OR_{8'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —$C(O)OR_8$, —$C(O)NR_8R_{8'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ and $R_{4'}$ form together with the carbon to which they are attached, a C=O group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ are independently selected from hydrogen, or substituted or unsubstituted $C_{1-6}$ alkyl, substituted or unsubstituted $C_{2-6}$ alkenyl, and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl and substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{7'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{7'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$, $R_{8'}$ and $R_{8''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$, $R_{8'}$ and $R_{8''}$ are independently selected from hydrogen, unsubstituted $C_{1-6}$ alkyl, unsubstituted $C_{2-6}$ alkenyl, and unsubstituted $C_{2-6}$ alkynyl; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{10}$, and $R_{10'}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_1$-6 alkyl, unsubstituted $C_{2-6}$ alkenyl, unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_1$-6 alkyl, unsubstituted $C_{2-6}$ alkenyl, unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$, $R_{13'}$ and $R_{13''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$, $R_{13'}$ and $R_{13''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_7$, —C(O)NR$_7$R$_{7'}$, —NR$_7$C(O)R$_{7'}$, and —NR$_7$R$_{7'''}$;

$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_7$, —C(O)NR$_7$R$_{7'}$, —NR$_7$C(O)R$_{7'}$, and —NR$_7$R$_{7'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is —C(R$_x$R$_x$)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is —CH$_2$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein m is 0, 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein p is 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, p is 1, X is a bond, and $R_2$ is substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, m is 0, p is 1, X is a bond and $R_1$ is hydrogen, substituted or unsubstituted methyl or substituted or unsubstituted ethyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, m is 0, p is 1, X is a bond, and $R_1$ is $C(O)R_6$, wherein $R_6$ is substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, m is 0, p is 1, X is a bond, $R_1$ is hydrogen, substituted or unsubstituted methyl or substituted or unsubstituted ethyl, and $R_2$ is substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, m is 0, p is 1, X is a bond, $R_1$ is is —$C(O)R_6$, and $R_2$ is substituted or unsubstituted phenyl; wherein $R_6$ is substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ and $R_{4'}$ form, together with the atom to which they are attached, a —C=O group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ and $R_{4'}$ are both hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 0, 1, 2, 3 or 4, preferably n is 0 or 1; and/or
m is 0, 1, 2, 3, 4, 5 or 6; preferably m is 0, 1 or 2, and/or
p is 1, 2 or 3; preferably p is 1; and/or
X is selected from a bond, and —$CR_xR_{x'}$;
and/or
$R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —$C(O)R_6$, —$C(O)OR_6$, —$C(O)NR_6R_{6'}$ and —$S(O)_2R_6$; more preferably $R_1$ is is hydrogen, substituted or unsubstituted $C_{1-6}$ alkyl or —$C(O)R_6$; wherein the $C_{1-6}$ alkyl is preferably selected from methyl, ethyl, propyl, butyl, pentyl, hexyl, isopropyl, isobutyl or 2-methylpropyl, more preferably the alkyl is methyl or ethyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
and/or
the aryl is selected from phenyl, naphtyl, or anthracene; preferably is napthyl and phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzo xazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_2$ is selected from substituted or unsubstituted monocyclic $C_{3-7}$ cycloalkyl, substituted or unsubstituted monocyclic aryl and substituted or unsubstituted monocyclic heterocyclyl;

wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_3$ is selected from hydrogen, halogen, —$R_9$, —$OR_9$, —$NO_2$, —$NR_9R_{9'''}$, —$NR_9C(O)R_{9'}$, —$NR_9S(O)_2R_{9'}$, —$S(O)_2NR_9R_{9'}$, —$NR_9C(O)NR_9R_{9''}$, —$SR_9$, —$S(O)R_9$, $S(O)_2R_9$, —CN, haloalkyl, haloalkoxy, —$C(O)OR_9$, —$C(O)NR_9R_{9'}$, —$NR_9S(O)_2NR_9R_{9''}$ and —$OC(O)R_9$;

$R_{3'}$, $R_{3''}$ and $R_{3'''}$ are independently selected from hydrogen, halogen, —$R_9$, —$OR_9$, —$NO_2$, —$NR_9R_{9'''}$, —$NR_9C(O)R_{9'}$, —$NR_9S(O)_2R_{9'}$, —$S(O)_2NR_9R_{9'}$, —$NR_9C(O)NR_9R_{9''}$, —$SR_9$, —$S(O)R_9$, $S(O)_2R_9$, —CN, haloalkyl, haloalkoxy, —$C(O)OR_9$, —$C(O)NR_9R_{9'}$, —$NR_9S(O)_2NR_9R_{9''}$ and —$OC(O)R_9$;

wherein the haloalkyl is $C_{1-4}$ haloalkyl, preferably $C_{1-3}$ haloalkyl, more preferably $C_{1-2}$ haloalkyl, even more preferably $C_1$ haloalkyl;

and/or the haloalkoxy is $C_{1-4}$ haloalkoxy, preferably $C_{1-3}$ haloalkoxy, more preferably $C_{1-2}$ haloalkoxy, even more preferably $C_1$ haloalkoxy;

and/or $R_4$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —$C(O)OR_8$, —$C(O)NR_8R_{8'}$, $R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl; wherein the $C_{1-6}$ alkyl is preferably selected from methyl, ethyl, propyl, butyl, pentyl, hexyl, isopropyl, isobutyl or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_5$ and $R_{5'}$ are independently selected from hydrogen, or substituted or unsubstituted $C_{1-6}$ alkyl, substituted or unsubstituted $C_{2-6}$ alkenyl, and substituted or unsubstituted $C_{2-6}$ alkynyl; wherein the $C_{1-6}$ alkyl is preferably selected from methyl, ethyl, propyl, butyl, pentyl, hexyl, isopropyl, isobutyl or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or wherein $R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl, isobutyl or 2-methylpropyl, more preferably the alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;

$R_{7'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, isobutyl or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_8$, $R_{8'}$ and $R_{8''}$ are independently selected from hydrogen, unsubstituted $C_{1-6}$ alkyl, unsubstituted $C_{2-6}$ alkenyl, and unsubstituted $C_{2-6}$ alkynyl;

$R_{8'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, isobutyl or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

$R_{9'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, isobutyl or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{10}$ and $R_{10'}$ are independently selected from hydrogen, unsubstituted $C_{1-6}$ alkyl, unsubstituted $C_{2-6}$ alkenyl, and unsubstituted $C_{2-6}$ alkynyl; wherein the $C_{1-6}$ alkyl is preferably selected from methyl, ethyl, propyl, butyl, pentyl, hexyl, isopropyl, isobutyl or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_7$, —C(O)NR$_7$R$_{7'}$, —NR$_7$C(O)R$_{7'}$, and —NR$_7$R$_{7'''}$; wherein the $C_{1-6}$ alkyl is preferably selected from methyl, ethyl, propyl, butyl, pentyl, hexyl, isopropyl, isobutyl or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl; wherein the $C_{1-6}$ alkyl is preferably selected from methyl, ethyl, propyl, butyl, pentyl, hexyl, isopropyl, isobutyl or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from like methyl, ethyl, propyl, butyl, pentyl, hexyl, isopropyl, isobutyl or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, isobutyl or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{13}$, $R_{13'}$ and $R_{13''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, isobutyl or 2-methylpropyl;

and/or the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_1$ as defined in any of the embodiments of the present invention,
the $C_{1-6}$ alkyl is preferably selected from methyl, ethyl, propyl, butyl, pentyl, hexyl, isopropyl, isobutyl or 2-methylpropyl, more preferably the alkyl is methyl or ethyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
and/or
the aryl is selected from phenyl, naphtyl, and anthracene; preferably is napthyl and phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or
the cycloalkyl is $C_m$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_2$ as defined in any of the embodiments of the present invention,
the aryl is selected from phenyl, naphtyl, or anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or
the cycloalkyl is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_x$ as defined in any of the embodiments of the present invention,
the $C_{1-6}$ alkyl is preferably selected from methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{x'}$ as defined in any of the embodiments of the present invention,
the $C_{1-6}$ alkyl is preferably selected from methyl, ethyl, propyl, butyl, pentyl, hexyl, isopropyl, isobutyl or 2-methylpropyl;
and/or the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_3$ as defined in any of the embodiments of the present invention,
the haloalkyl is $C_{1-4}$ haloalkyl, preferably $C_{1-3}$ haloalkyl, more preferably $C_{1-2}$ haloalkyl, even more preferably $C_1$ haloalkyl;
and/or
the haloalkoxy is $C_{1-4}$ haloalkoxy, preferably $C_{1-3}$ haloalkoxy, more preferably $C_{1-2}$ haloalkoxy, even more preferably $C_1$ haloalkoxy;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{3'}$, $R_{3''}$ and $R_{3'''}$ as defined in any of the embodiments of the present invention,
the haloalkyl is $C_{1-4}$ haloalkyl, preferably $C_{1-3}$ haloalkyl, more preferably $C_{1-2}$ haloalkyl, even more preferably $C_1$ haloalkyl;
and/or
the haloalkoxy is $C_{1-4}$ haloalkoxy, preferably $C_{1-3}$ haloalkoxy, more preferably $C_{1-2}$ haloalkoxy, even more preferably $C_1$ haloalkoxy;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_4$ as defined in any of the embodiments of the present invention,
the $C_{1-6}$ alkyl is preferably selected from methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{4'}$ as defined in any of the embodiments of the present invention,
the $C_{1-6}$ alkyl is preferably selected from like methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_5$ as defined in any of the embodiments of the present invention,
the $C_{1-6}$ alkyl is preferably selected from methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_5$ as defined in any of the embodiments of the present invention,
the $C_{1-6}$ alkyl is preferably selected from methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_6$ as defined in any of the embodiments of the present invention, the $C_{1-6}$ alkyl is preferably selected from methyl, ethyl, propyl, butyl, pentyl, hexyl, isopropyl, isobutyl or 2-methylpropyl, more preferably the alkyl is methyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{6'}$ as defined in any of the embodiments of the present invention, the $C_{1-6}$ alkyl is preferably selected from methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_7$, $R_{7'}$ and $R_{7''}$ as defined in any of the embodiments of the present invention, the $C_{1-6}$ alkyl is preferably selected from methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{7'''}$ as defined in any of the embodiments of the present invention, the $C_{1-6}$ alkyl is preferably selected from methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_8$, $R_{8'}$ and $R_{8''}$ as defined in any of the embodiments of the present invention, the $C_{1-6}$ alkyl is preferably selected from methyl, ethyl, propyl, butyl, pentyl, hexyl, isopropyl, isobutyl or 2-methylpropyl;
and/or the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{8'''}$ as defined in any of the embodiments of the present invention,
the $C_{1-6}$ alkyl is preferably selected from methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_9$, $R_{9'}$ and $R_{9''}$ as defined in any of the embodiments of the present invention,
the $C_{1-6}$ alkyl is preferably selected from methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{9'''}$ as defined in any of the embodiments of the present invention,
the $C_{1-6}$ alkyl is preferably selected from methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{10}$ as defined in any of the embodiments of the present invention,
the $C_{1-6}$ alkyl is preferably selected from methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{10'}$ as defined in any of the embodiments of the present invention,
the $C_{1-6}$ alkyl is preferably selected from like methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11}$, $R_{11'}$ and $R_{11''}$ as defined in any of the embodiments of the present invention,
the $C_{1-6}$ alkyl is preferably selected from methyl, ethyl, propyl, butyl, pentyl, hexyl, isopropyl, isobutyl or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11'''}$ as defined in any of the embodiments of the present invention,
- the $C_{1-6}$ alkyl is preferably selected from methyl, ethyl, propyl, butyl, pentyl, hexyl, isopropyl, isobutyl or 2-methylpropyl;

and/or
- the $C_{2-6}$-alkenyl is preferably selected from ethylene, propylene, butylene, pentylene, hexylene, isopropylene and isobutylene;

and/or
- the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12}$, $R_{12'}$ and $R_{12''}$ as defined in any of the embodiments of the present invention,
- the $C_{1-6}$ alkyl is preferably selected from methyl, ethyl, propyl, butyl, pentyl, hexyl, isopropyl, isobutyl or 2-methylpropyl;

and/or
- the $C_{2-6}$-alkenyl is preferably selected from ethylene, propylene, butylene, pentylene, hexylene, isopropylene and isobutylene;

and/or
- the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12'''}$ as defined in any of the embodiments of the present invention,
- the $C_{1-6}$ alkyl is preferably selected from methyl, ethyl, propyl, butyl, pentyl, hexyl, isopropyl, isobutyl or 2-methylpropyl;

and/or
- the $C_{2-6}$-alkenyl is preferably selected from ethylene, propylene, butylene, pentylene, hexylene, isopropylene and isobutylene;

and/or
- the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13}$, $R_{13'}$ and $R_{13''}$ as defined in any of the embodiments of the present invention,
- the $C_{1-6}$ alkyl is preferably selected from methyl, ethyl, propyl, butyl, pentyl, hexyl, isopropyl, isobutyl or 2-methylpropyl;

and/or
- the $C_{2-6}$-alkenyl is preferably selected from ethylene, propylene, butylene, pentylene, hexylene, isopropylene and isobutylene;

and/or
- the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13'''}$ as defined in any of the embodiments of the present invention,
- the $C_{1-6}$ alkyl is preferably selected from methyl, ethyl, propyl, butyl, pentyl, hexyl, isopropyl, isobutyl or 2-methylpropyl;

and/or
- the $C_{2-6}$-alkenyl is preferably selected from ethylene, propylene, butylene, pentylene, hexylene, isopropylene and isobutylene;

and/or
- the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
n is 0, 1, 2, 3 or 4, preferably n is 0 or 1;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
m is 0, 1, 2, 3, 4, 5 or 6; preferably m is 0, 1 or 2;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein p is 1, 2 or 3; preferably p is 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein X is selected from a bond, and —$CR_xR_{x'}$; preferably, X is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 0, 1, 2 and/or n is 0, 1 and/or p is 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_1$ is selected from hydrogen, substituted or unsubstituted $C_{1-6}$ alkyl, preferably substituted or unsubstituted methyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl and —C(O)$R_6$, and wherein $R_6$ and $R_{6'}$ are independently selected from hydrogen, substituted or unsubstituted $C_{1-6}$ alkyl, preferably substituted or unsubstituted methyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_2$ is substituted or unsubstituted monocyclic aryl, preferably substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein X is selected from a bond and —$C(R_xR_{x'})$—; and wherein $R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl;

$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein X is selected from a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_3$, $R_{3'}$, $R_{3''}$ and $R_{3'''}$ are independently selected from hydrogen, halogen, —$R_9$, —$OR_9$ and —$NR_9R_{9'''}$, and wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_4$ is selected from hydrogen, substituted or unsubstituted $C_{1-6}$ alkyl, substituted or unsubstituted $C_{2-6}$ alkenyl and substituted or unsubstituted $C_{2-6}$ alkynyl, $R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl; or $R_4$ and $R_{4'}$ may form together with the carbon to which they are attached, a C=O group.

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 0, 1 or 2; and n is 0 or 1; and p is 1; and $R_1$ is selected from hydrogen, substituted or unsubstituted $C_{1-6}$ alkyl, preferably substituted or unsubstituted methyl and —C(O)R$_6$; wherein R$_6$ is substituted or unsubstituted C$_{1-6}$ alkyl, preferably substituted or unsubstituted methyl; and R$_2$ is substituted or unsubstituted monocyclic aryl, preferably substituted or unsubstituted phenyl; and X is a bond; and R$_3$, R$_{3'}$, R$_{3''}$ and R$_{3'''}$ are all hydrogen; and R$_4$ and R$_{4'}$ are both hydrogen, or R$_4$ and R$_{4'}$ may form together with the carbon to which they are attached, a C=O group; and R$_5$ and R$_{5'}$ are both hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a particular embodiment of this preferred embodiment, the following proviso applies:

when R$_4$ is hydrogen and R$_1$ is C(O)R$_6$, then n is 1.

In a particular embodiment the following compound is excluded:

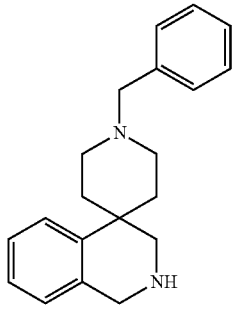 [SMILES: c1ccc(CN2CCC3(CC2)CNCc2ccccc23)cc1]

In a further preferred embodiment of the invention according to general Formula (I) the compound is a compound, wherein m is 0, 1 or 2; and/or n is 0 or 1; and/or p is 1; and/or R$_1$ is selected from hydrogen, substituted or unsubstituted C$_{1-6}$ alkyl, preferably substituted or unsubstituted methyl and —C(O)R$_6$; wherein R$_6$ is substituted or unsubstituted C$_{1-6}$ alkyl, preferably substituted or unsubstituted methyl; and/or R$_2$ is substituted or unsubstituted monocyclic aryl, preferably substituted or unsubstituted phenyl; and/or X is a bond; and/or R$_3$, R$_{3'}$, R$_{3''}$ and R$_{3'''}$ are all hydrogen; and/or R$_4$ and R$_{4'}$ are both hydrogen, or R$_4$ and R$_{4'}$ may form together with the carbon to which they are attached, a C=O group; and/or R$_5$ and R$_{5'}$ are both hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 0 or 1; and n is 0 or 1; and p is 1; and R$_1$ is selected from hydrogen, substituted or unsubstituted C$_{1-6}$ alkyl, preferably substituted or unsubstituted methyl and —C(O)R$_6$; wherein R$_6$ is substituted or unsubstituted C$_{1-6}$ alkyl, preferably substituted or unsubstituted methyl; and R$_2$ is substituted or unsubstituted monocyclic aryl, preferably substituted or unsubstituted phenyl; and X is a bond; and R$_3$, R$_{3'}$, R$_{3''}$ and R$_{3'''}$ are all hydrogen; and R$_4$ and R$_{4'}$ form together with the carbon to which they are attached, a C=O group; and R$_5$ and R$_{5'}$ are both hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment

R$_1$ is hydrogen or a substituted or unsubstituted group selected from methyl, ethyl and acetyl; preferably R$_1$ is hydrogen, unsubstituted methyl, unsubstituted ethyl or unsubstituted acetyl.

In another preferred embodiment

R$_1$ is hydrogen or a substituted or unsubstituted group selected from methyl and ethyl, preferably R$_1$ is hydrogen, unsubstituted methyl or unsubstituted ethyl.

In a preferred embodiment

R$_2$ is a substituted or unsubstituted phenyl.

In a preferred embodiment

R$_3$ is hydrogen.

In a preferred embodiment

R$_{3'}$, R$_{3''}$ and R$_{3'''}$ are all hydrogen.

In a preferred embodiment

R$_3$, R$_{3'}$, R$_{3''}$ and R$_{3'''}$ are all hydrogen.

In a preferred embodiment

R$_4$ and R$_{4'}$ are both hydrogen.

In a preferred embodiment

R$_4$ and R$_{4'}$ form together with the carbon to which they are attached a C=O group.

In a preferred embodiment

R$_5$ and R$_{5'}$ are both hydrogen.

In a preferred embodiment

R$_6$ is substituted or unsubstituted methyl, preferably unsubstituted methyl.

In a preferred embodiment

R$_x$ is hydrogen.

In a preferred embodiment

R$_x$' is hydrogen.

In a preferred embodiment

R$_x$ and R$_x$' are both hydrogen.

In another preferred embodiment n is 0 or 1.

In another preferred embodiment m is 0, 1 or 2.

In another preferred embodiment m is 0 or 1.

In another preferred embodiment p is 1.

In another preferred embodiment

X is a bond or —CH$_2$—.

In an particular embodiment the halogen is fluorine, chlorine, iodine or bromine.

In an particular embodiment the halogen is fluorine or chlorine.

In a preferred further embodiment, the compounds of the general Formula (I) are selected from

| EX | Chemical name |
|---|---|
| 1 | 1'-benzyl-2,3-dihydro-1H-spiro[isoquinoline-4,4'-piperidin]-1-one |
| 2 | 1'-benzyl-2-methyl-2,3-dihydro-1H-spiro[isoquinoline-4,4'-piperidin]-1-one |
| 3 | 1'-benzyl-2-ethyl-2,3-dihydro-1H-spiro[isoquinoline-4,4'-piperidin]-1-one |
| 4 | 1'-phenethyl-2,3-dihydro-1H-spiro[isoquinoline-4,4'-piperidin]-1-one |
| 5 | 2-methyl-1'-phenethyl-2,3-dihydro-1H-spiro[isoquinoline-4,4'-piperidin]-1-one |
| 6 | 2-ethyl-1'-phenethyl-2,3-dihydro-1H-spiro[isoquinoline-4,4'-piperidin]-1-one |
| 7 | 1'-benzyl-2-(2-hydroxyethyl)-2,3-dihydro-1H-spiro[isoquinoline-4,4'-piperidin]-1-one |
| 8 | 1'-phenethyl-2,3-dihydro-1H-spiro[isoquinoline-4,4'-piperidine] |
| 9 | 2-methyl-1'-phenethyl-2,3-dihydro-1H-spiro[isoquinoline-4,4'-piperidine] |
| 10 | 1-(1'-phenethyl-1H-spiro[isoquinoline-4,4'-piperidine]-2(3H)-yl)ethanone |
| 11 | 2-(2-hydroxyethyl)-1'-phenethyl-2,3-dihydro-1H-spiro[isoquinoline-4,4'-piperidin]-1-one | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred further embodiment, the compounds of the general Formula (I) are selected from

| EX | Chemical name |
|---|---|
| 1 | 1'-benzyl-2,3-dihydro-1H-spiro[isoquinoline-4,4'-piperidin]-1-one |
| 2 | 1'-benzyl-2-methyl-2,3-dihydro-1H-spiro[isoquinoline-4,4'-piperidin]-1-one |
| 3 | 1'-benzyl-2-ethyl-2,3-dihydro-1H-spiro[isoquinoline-4,4'-piperidin]-1-one |
| 4 | 1'-phenethyl-2,3-dihydro-1H-spiro[isoquinoline-4,4'-piperidin]-1-one |
| 5 | 2-methyl-1'-phenethyl-2,3-dihydro-1H-spiro[isoquinoline-4,4'-piperidin]-1-one |
| 6 | 2-ethyl-1'-phenethyl-2,3-dihydro-1H-spiro[isoquinoline-4,4'-piperidin]-1-one |
| 7 | 1'-benzyl-2-(2-hydroxyethyl)-2,3-dihydro-1H-spiro[isoquinoline-4,4'-piperidin]-1-one |
| 11 | 2-(2-hydroxyethyl)-1'-phenethyl-2,3-dihydro-1H-spiro[isoquinoline-4,4'-piperidin]-1-one | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I), is a compound wherein n is 1, p is 1, X is a bond, and $R_2$ is substituted or unsubstituted phenyl, the compound being exemplified in examples 4, 5, 6, 8, 9, 10, 11;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I), is a compound wherein n is 1, m is 0, p is 1, X is a bond and $R_1$ is hydrogen, substituted or unsubstituted methyl or substituted or unsubstituted ethyl, the compound being exemplified in examples 4, 5, 6, 8, 9 and 11;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I), is a compound wherein n is 0, m is 0, p is 1, X is a bond and $R_1$ is hydrogen, substituted or unsubstituted methyl or substituted or unsubstituted ethyl, the compound being exemplified in examples 1, 2, 3 and 7;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein n is 1, m is 0, p is 1, X is a bond, and $R_1$ is —C(O)$R_6$, wherein $R_6$ is substituted or unsubstituted methyl, the compound being exemplified in example 10;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein n is 1, m is 0, p is 1, X is a bond, $R_1$ is hydrogen, substituted or unsubstituted methyl or substituted or unsubstituted ethyl, and $R_2$ is substituted or unsubstituted phenyl, the compound being exemplified in examples 4, 5, 6, 8, 9 and 11;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein n is 1, m is 0, p is 1, X is a bond, $R_1$ is is —(O)$R_6$, and $R_2$ is substituted or unsubstituted phenyl; wherein $R_6$ is substituted or unsubstituted methyl, the compound being exemplified in examples 10;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein $R_4$ and $R_{4'}$ form, together with the atom to which they are attached, a —C=O group, the compound being exemplified in examples 1 to 7 and 11;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein $R_4$ and $R_{4'}$ are both hydrogen, the compound being exemplified in examples 8 to 10;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), $R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —C(O)$R_6$, —C(O)O$R_6$, —C(O)N$R_6R_{6'}$ and —S(O)$_2R_6$;

wherein $R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein said cycloalkyl, aryl or heterocyclyl in $R_1$, if substituted, is substituted with one or more substituent/s selected from halogen, —$R_{11}$, —O$R_{11}$, —NO$_2$, —N$R_{11}R_{11'''}$, N$R_{11}$C(O)$R_{11'}$, —N$R_{11}$S(O)$_2R_{11'}$, —S(O)$_2$N$R_{11}R_{11'}$, —N$R_{11}$C(O)N$R_{11'}R_{11''}$, —S$R_{11}$, —S(O)$R_{11}$, S(O)$_2R_{11}$, —CN, haloalkyl, haloalkoxy, —C(O)O$R_{11}$, —C(O)N$R_{11}R_{11'}$, and N$R_{11}$S(O)$_2$N$R_{11'}R_{11''}$;

wherein the cycloalkyl or non-aromatic heterocyclyl in $R_1$ or $R_6$, if substituted, may also be substituted with

or =O;

wherein the alkyl, alkenyl or alkynyl in $R_1$ or $R_6$, if substituted, is substituted with one or more substituent/s selected from —O$R_{11}$, halogen, —CN, haloalkyl, haloalkoxy, —S$R_{11}$, —S(O)$R_{11}$, and —S(O)$_2R_{11}$;

wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), $R_2$ is selected from substituted or unsubstituted monocyclic $C_{3-7}$ cycloalkyl, substituted or unsubstituted monocyclic aryl and substituted or unsubstituted monocyclic heterocyclyl;

wherein said cycloalkyl, aryl or heterocyclyl in $R_2$, if substituted, is substituted with one or more substituent/s selected from halogen, —$R_{12}$, —O$R_{12}$, —NO$_2$, —N$R_{12}R_{12'''}$, —N$R_{12}$C(O)$R_{12'}$, —N$R_{12}$S(O)$_2R_{12'}$, —S(O)$_2$N$R_{12}R_{12'}$, —N$R_{12}$C(O)N$R_{12'}R_{12''}$, —S$R_{12}$, —S(O)$R_{12}$, S(O)$_2R_{12}$, —CN, haloalkyl, haloalkoxy, —C(O)O$R_{12}$, —C(O)N$R_{12}R_{12'}$, —N$R_{12}$S(O)$_2$N$R_{12'}R_{12''}$;

wherein the cycloalkyl or non-aromatic heterocyclyl in $R_2$, if substituted, may also be substituted with

or =O;

wherein $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the alkyl, alkenyl or alkynyl, other than those defined in $R_1$, $R_2$ or $R_6$, if substituted, is substituted with one or more substituent/s selected from —O$R_{10}$, halogen, —CN, haloalkyl, haloalkoxy, —S$R_{10}$, —S(O)$R_{10}$, and —S(O)$_2R_{10}$;

wherein $R_{10}$ and $R_{10'}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the aryl, heterocyclyl or cycloalkyl, other than those defined in $R_1$, $R_2$ or $R_6$, if substituted, is substituted with one or more substituent/s selected from halogen, —$R_{13}$, —O$R_{13}$, —NO$_2$, —N$R_{13}R_{13'''}$, N$R_{13}$C(O)$R_{13'}$, —N$R_{13}$S(O)$_2R_{13'}$, —S(O)$_2$N$R_{13}R_{13'}$, —N$R_{13}$C(O)N$R_{13'}R_{13''}$, —S$R_{13}$, —S(O)$R_{13}$, S(O)$_2R_{13}$, —CN, haloalkyl, haloalkoxy, —C(O)O$R_{13}$, —C(O)N$R_{13}R_{13'}$ and —N$R_{13}$S(O)$_2$N$R_{13'}R_{13''}$;

wherein cycloalkyl or non-aromatic heterocyclyl, other than those defined in $R_1$, $R_2$ or $R_6$, if substituted, may also be substituted with

or =O;
wherein $R_{13}$, $R_{13'}$ and $R_{13''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the embodiments of the present invention,
the cycloalkyl, aryl or heterocyclyl in $R_1$, if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, and $NR_{11}S(O)_2NR_{11'}R_{11''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_6$ of any of the embodiments of the present invention,
the heterocyclyl in $R_6$, if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, and $NR_{11}S(O)_2NR_{11'}R_{11''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the embodiments of the present invention,
the cycloalkyl or non-aromatic heterocyclyl in $R_1$, if substituted, may also be substituted with

or =O;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_6$ of any of the embodiments of the present invention,
the non-aromatic heterocyclyl in $R_6$, if substituted, may also be substituted with

or =O;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention,
the cycloalkyl, aryl or heterocyclyl in $R_2$, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, and —$NR_{12}S(O)_2NR_{12'}R_{12''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention,
the cycloalkyl or non-aromatic heterocyclyl in $R_2$, if substituted, may also be substituted with

or =O;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to alkyls other than those defined in $R_1$, $R_2$ or $R_6$ of any of the embodiments of the present invention,
the alkyl, alkenyl or alkynyl, other than those defined in $R_1$, $R_2$ or $R_6$, if substituted, is substituted with one or more substituent/s selected from —$OR_{10}$, halogen, —CN, haloalkyl, haloalkoxy, —$SR_{10}$, —S—$(O)R_{10}$, and —$S(O)_2R_{10}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to the cycloalkyl, aryl or heterocyclyl other than those defined in $R_1$, $R_2$ or $R_6$ of any of the embodiments of the present invention, the aryl, heterocyclyl or cycloalkyl, other than those defined in $R_1$, $R_2$ or $R_6$, if substituted, is substituted with one or more substituent/s selected from halogen, $—R_{13}$, $—OR_{13}$, $—NO_2$, $—NR_{13}R_{13'''}$, $—NR_{13}C(O)R_{13'}$, $—NR_{13}S(O)_2R_{13'}$, $—S(O)_2NR_{13}R_{13'}$, $—NR_{13}C(O)NR_{13'}R_{13''}$, $—SR_{13}$, $—S(O)R_{13}$, $S(O)_2R_{13}$, $—CN$, haloalkyl, haloalkoxy, $—C(O)OR_{13}$, $—C(O)NR_{13}R_{13'}$, $—NR_{13}S(O)_2NR_{13'}R_{13''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to to the cycloalkyl, aryl or heterocyclyl other than those defined in $R_1$, $R_2$ or $R_6$ of any of the embodiments of the present invention, the cycloalkyl or non-aromatic heterocyclyl, other than those defined in $R_1$, $R_2$ or $R_6$, if substituted, may also be substituted with

or $=O$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I), the halogen is fluorine, chlorine, iodine or bromine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a most preferred embodiment of the compound according to the invention of general Formula (I)

the halogen is fluorine or chlorine optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I), the haloalkyl is $—CF3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the compound according to the invention of general Formula (I), the haloalkoxy is $—OCF3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as dual ligands of the $\sigma_1$ receptor and the µ-opiod receptor it is a very preferred embodiment in which the compounds are selected which act as dual ligands of the $\sigma_1$ receptor and the µ-opiod receptor and especially compounds which have a binding expressed as $K_i$ which is preferably <1000 nM for both receptors, more preferably <500 nM, even more preferably <100 nM.

In the following the phrase "compound of the invention" is used. This is to be understood as any compound according to the invention as described above according to general Formula (I), (I'), ($I^{2'}$), ($I^{3'}$) or ($I^{4'}$) or ($I^{5'}$).

The compounds of the invention represented by the above described Formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

A preferred aspect of the invention is also a process for the production of a compound according to Formula (I), following scheme 1.

A preferred embodiment of the invention is a process for the production of a compound according to Formula (I), wherein $R_1$, $R_2$, $R_3$, $R_{3'}$, $R_{3''}$, $R_{3'''}$, $R_4$, $R_{4'}$, $R_5$, $R_{5'}$, X, m, n and p are as defined in the description, following scheme 1.

For the sake of clarity the expression "a compound according to Formula (I), wherein $R_1$, $R_2$, $R_3$, $R_{3'}$, $R_{3''}$, $R_{3'''}$, $R_4$, $R_{4'}$, $R_5$, $R_{5'}$, X, m, n and p are as defined in the description" would (just like the expression "a compound of Formula (I) as defined in any one of claims 1 to 10" found in the claims) refer to "a compound according to Formula (I)", wherein the definitions of the respective substituents R1 etc. (also from the cited claims) are applied. In addition, this would also mean, though (especially in regards to the claims) that also one or more disclaimers defined in the description (or used in any of the cited claims like e.g. claim 1) would be applicable to define the respective compound. Thus, a disclaimer found in e.g. claim 1 would be also used to define the compound "of Formula (I) as defined in any one of claims 1 to 10".

In a particular embodiment there is a process for the production of a compound of Formula (I),

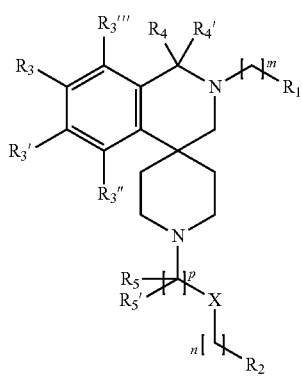 (I)

said process comprises reacting a compound of Formula (IX')

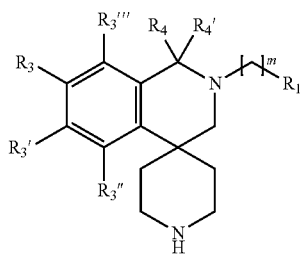 IX' with a compound of formula (Xa) through a reductive amination reaction or (Xb) through an alkylation reaction

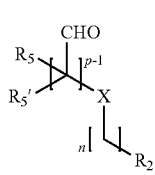 Xa

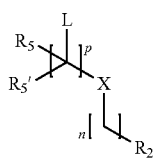 Xb following the general procedure of scheme 1, wherein $R_1$, $R_2$, $R_3$, $R_3'$, $R_3''$, $R_3'''$, $R_4$, $R_4'$, $R_5$, $R_5'$, X, m, n and p are as defined in the description and L is a leaving group such as chloro, bromo, mesylate or toxylate.

In a particular embodiment there is a process for the production of a compound of Formula (I),

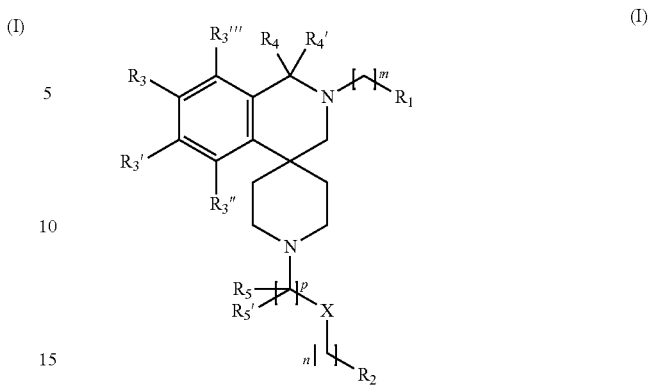 (I)

said process comprises N-alkylating a compound of Formula (Ia')

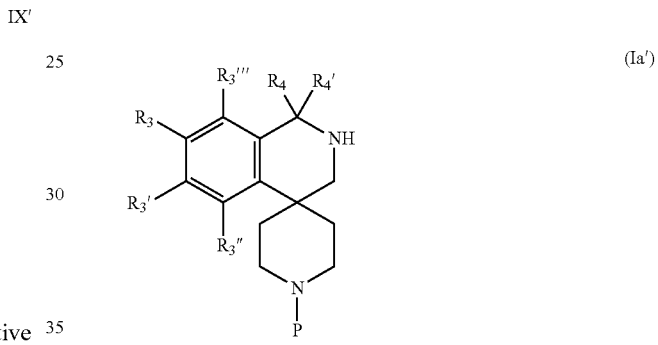 (Ia')

with a compound of Formula (VIa)

 VIa following STEP 3 of scheme 1, wherein P is

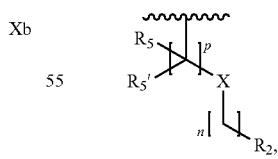

wherein $R_1$, $R_2$, $R_3$, $R_3'$, $R_3''$, $R_3'''$, $R_4$, $R_4'$, $R_5$, $R_5'$, X, m, n and p are as defined in the description and L is a leaving group such as chloro, bromo, mesylate or toxylate.

In a particular embodiment there is a process for the production of a compound of Formula (VII') or (Ib'),

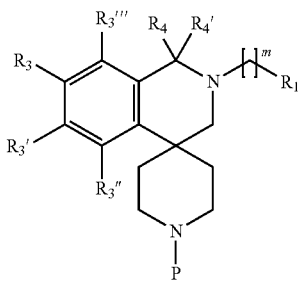

VII' (P═PG)

Ib' (P═Y)

said process comprises N-alkylating a compound of Formula (V') or (Ia'), respectively

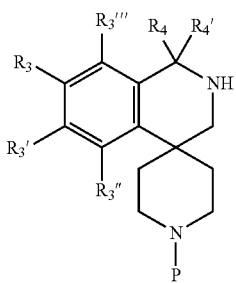

V' (P═PG)

Ia' (P═Y)

with a compound of Formula (VIa)

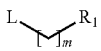

VIa following STEP 3 of scheme 1, wherein PG is a protecting group and Y is

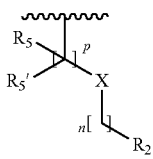

wherein $R_1$, $R_2$, $R_3$, $R_{3'}$, $R_{3''}$, $R_{3'''}$, $R_4$, $R_{4'}$, $R_5$, $R_{5'}$, X, m, n and p are as defined in the description and L is a leaving group such as chloro, bromo, mesylate or toxylate.

In a particular embodiment there is a process for the production of a compound of Formula (I),

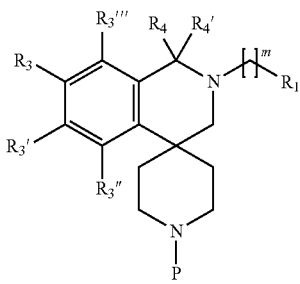

VII' (P═PG)

Ib' (P═Y)

said process comprises reacting a compound of Formula (IX')

IX'

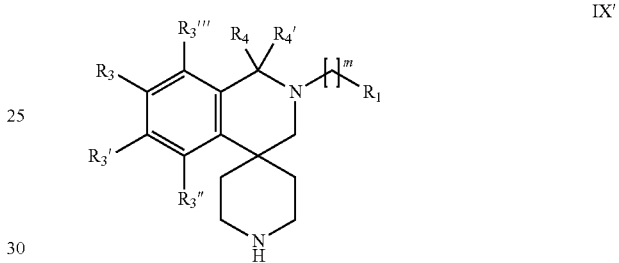

with a compound of formula (Xa) through a reductive amination reaction or (Xb) through an alkylation reaction

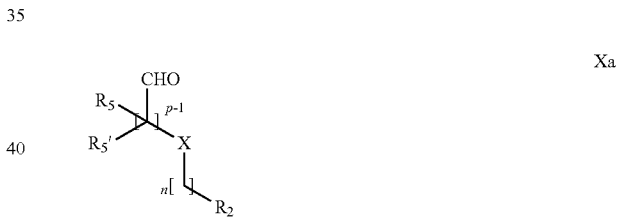

Xa

Xb

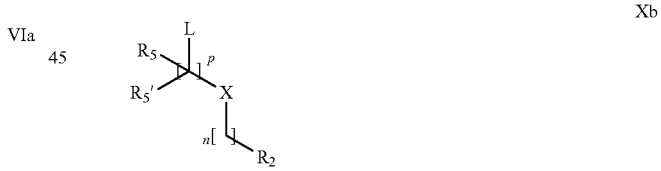

wherein PG is a protecting group and Y is

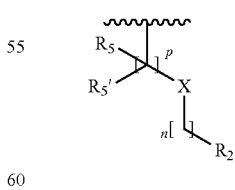

following the general procedure of scheme 1, wherein $R_1$, $R_2$, $R_3$, $R_{3'}$, $R_{3''}$, $R_{3'''}$, $R_4$, $R_{4'}$, $R_5$, $R_{5'}$, X, m, n and p are as defined in the description and L is a leaving group such as chloro, bromo, mesylate or toxylate.

In a particular embodiment there is a process for the production of a compound of Formula (V') or (Ia')

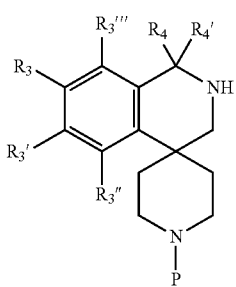

V' (P=PG)

Ia' (P=Y)

wherein PG is a protecting group and Y is

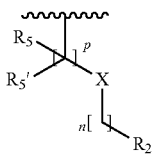

following the general procedure of scheme 1, wherein $R_2$, $R_3$, $R_3'$, $R_3''$, $R_3'''$, $R_4$, $R_4'$, $R_5$, $R_5'$, X, n and p are as defined in the description and L is a leaving group such as chloro, bromo, mesylate or toxylate.

In a particular embodiment there is a process for the production of a compound of Formula (Id')

Id'

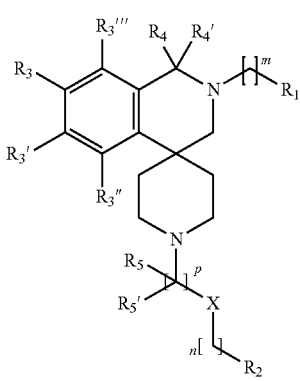

wherein PG is a protecting group and Y is

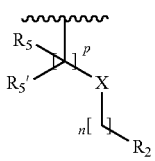

said process comprises reacting a compound of Formula (VIII')

comprising reacting compound of Formula (Ic')

Ic'

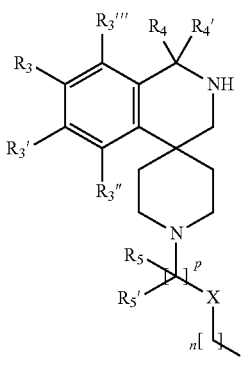

VIII'

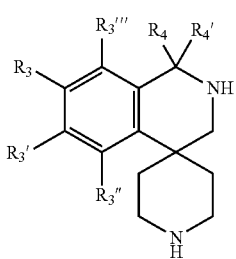

with a compound of Formula (Xa) through a reductive amination reaction or (Xb) through an alkylation reaction Xa

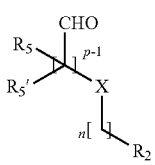

with a compound of Formula (VIa) through an alkylation reaction, a compound of Formula (VIb) through a reductive amination reaction or (VIc) or (VId) through an acylation reaction Xb

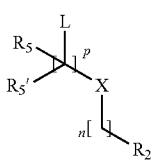

VIa

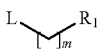

VIb

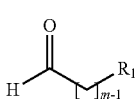

-continued

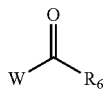

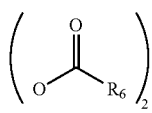

following STEP 5 of scheme 1, wherein $R_1$, $R_2$, $R_3$, $R_{3'}$, $R_{3''}$, $R_{3'''}$, $R_4$, $R_{4'}$, $R_5$, $R_{5'}$, $R_6$, X, m, n and p are as defined in the description, L is a leaving group such as chloro, bromo, mesylate or toxylate, and W is chloro, bromo, —OH, OMe, or OEt.

In a particular embodiment there is a process for the production of a compound of Formula (VII) or (Ib)

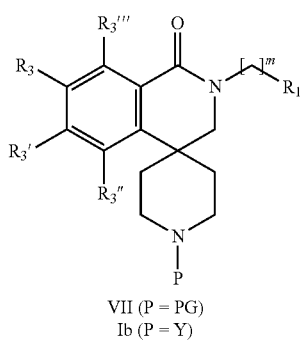

VII (P = PG)
Ib (P = Y)

said process comprises the N-alkylation of a compound of Formula (V) or (Ia) respectively,

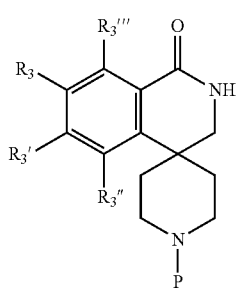

V (P = PG)
Ia (P = Y)

with a compound of Formula (VIa)

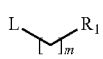

VIa wherein PG is a protecting group and Y is

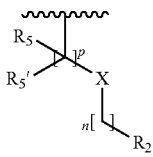

VIc following STEP 3 of scheme 1, wherein $R_1$, $R_2$, $R_3$, $R_{3'}$, $R_{3''}$, $R_{3'''}$, $R_4$, $R_{4'}$, $R_5$, $R_{5'}$, X, n and p are as defined in the description and L is a leaving group such as chloro, bromo, mesylate or toxylate.

In a particular embodiment there is a process for the production of a compound of Formula (V) or (Ia)

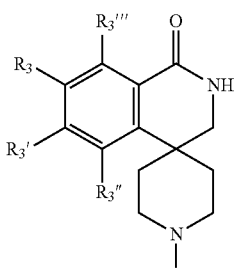

V (P = PG)
Ia (P = Y)

said process comprises the reduction of a compound of Formula (IVa) or (IVb) respectively,

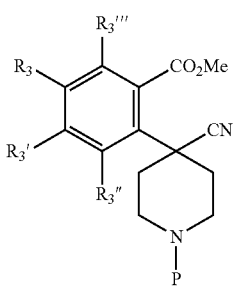

IVa (P = PG)
IVb (P = Y)

and subsequent cyclization of the generated intermediate amine compound, wherein PG is a protecting group and Y is

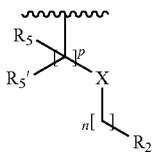

VIa following STEP 2 of scheme 1, wherein $R_2$, $R_3$, $R_{3'}$, $R_{3''}$, $R_{3'''}$, $R_5$, $R_{5'}$, X, n and p are as defined in the description.

In a particular embodiment there is a process for the production of a compound of Formula (IVa) or (IVb)

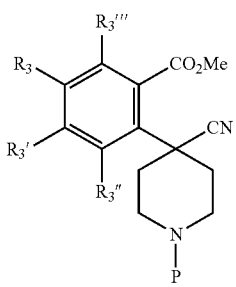

IVa (P = PG)
IVb (P = Y)

said process comprises treating a compound of Formula (II)

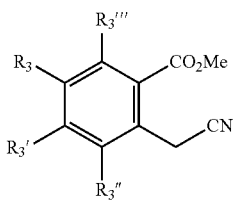

II with a strong base like NaH, and subsequently treating the resulting deprotonated intermediate with a compound of Formula (IIIa) or (IIIb), respectively,

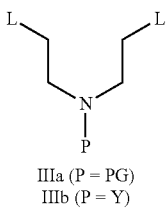

IIIa (P = PG)
IIIb (P = Y)

wherein PG is a protecting group and Y is

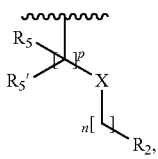

following STEP 1 of scheme 1, wherein $R_2$, $R_3$, $R_{3'}$, $R_{3''}$, $R_{3'''}$, $R_5$, $R_{5'}$, X, n and p are as defined in the description and L is a leaving group such as chloro, bromo, mesylate or toxylate.

In a particular embodiment there is a process for the production of a compound of Formula (Ic)

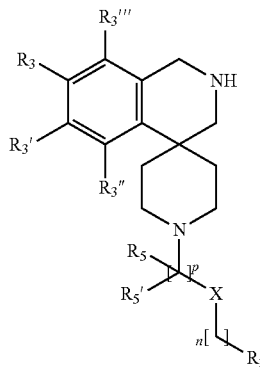

Ic comprising reducing a compound of Formula (Ia),

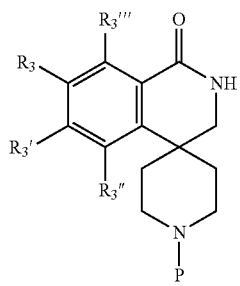

V (P = PG)
Ia (P = Y)

wherein P is

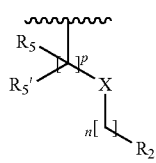

following STEP 4 of scheme 1, wherein $R_2$, $R_3$, $R_{3'}$, $R_{3''}$, $R_{3'''}$, $R_5$, $R_{5'}$, X, n and p are as defined in the description.

In a particular embodiment there is a process for the production of a compound of Formula (Id)

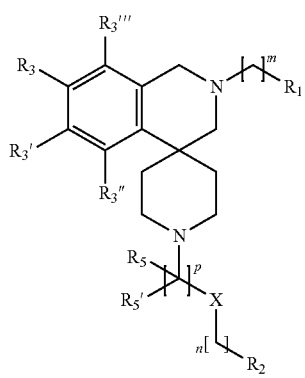

Id comprising reacting compound of Formula (Ic)

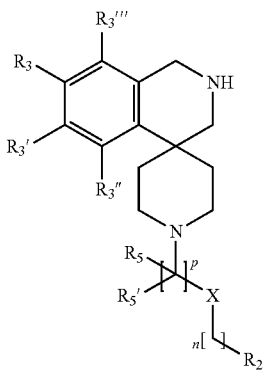

Ic with a compound of Formula (VIa) through an alkylation reaction, a compound of Formula (VIb) through a reductive amination reaction or (VIc) or (VId) through an acylation reaction

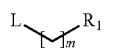

VIa

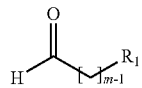

VIb

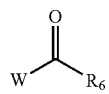

VIc

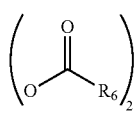

VId following STEP 5 of scheme 1, wherein $R_1$, $R_2$, $R_3$, $R_3'$, $R_3''$, $R_3'''$, $R_4$, $R_4'$, $R_5$, $R_5'$, $R_6$, X, m, n and p are as defined in the description, L is a leaving group such as chloro, bromo, mesylate or toxylate, and W is chloro, bromo, —OH, OMe, or OEt.

In a particular embodiment there is a process for the production of a compound of Formula (V) or (Ia)

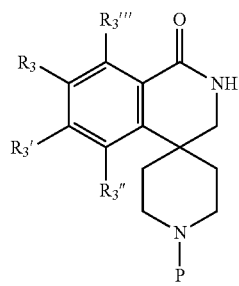

V (P = PG)
Ia (P = Y)

wherein PG is a protecting group and Y is

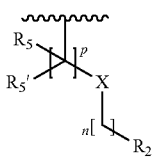

said process comprises reacting a compound of Formula (VIII)

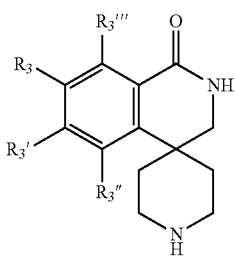

VIII with a compound of Formula (Xa) through a reductive amination reaction or (Xb) through an alkylation reaction

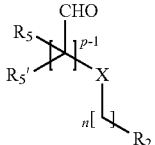

Xa

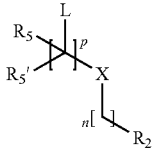

Xb wherein PG is a protecting group and Y is

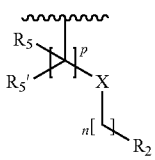

following the general procedure of scheme 1, wherein $R_2$, $R_3$, $R_3'$, $R_3''$, $R_3'''$, $R_4$, $R_4'$, $R_5$, $R_5'$, X, n and p are as defined in the description and L is a leaving group such as chloro, bromo, mesylate or toxylate.

In a particular embodiment there is a process for the production of a compound of Formula (Ib),

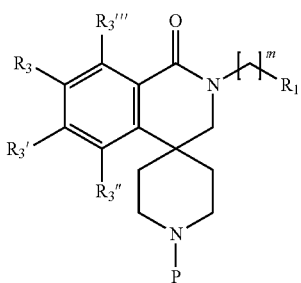

VII (P = PG)
Ib (P = Y)

said process comprises reacting a compound of Formula (IX)

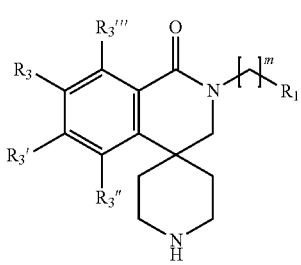

IX with a compound of formula (Xa) through a reductive amination reaction or (Xb) through an alkylation reaction

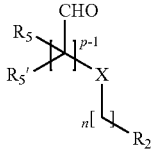

Xa

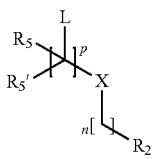

Xb wherein PG is a protecting group and Y is

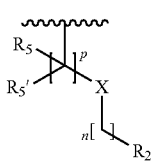

following the general procedure of scheme 1, wherein $R_1$, $R_2$, $R_3$, $R_{3'}$, $R_{3''}$, $R_{3'''}$, $R_4$, $R_{4'}$, $R_5$, $R_{5'}$, X, m, n and p are as defined in the description and L is a leaving group such as chloro, bromo, mesylate or toxylate.

In another particular embodiment a compound of Formula (Ia) or (V),

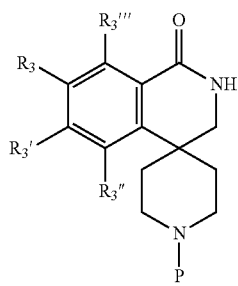

V (P = PG)
Ia (P = Y)

wherein PG is a protecting group and Y is

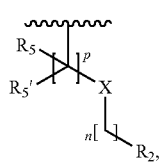

and wherein $R_2$, $R_3$, $R_{3'}$, $R_{3''}$, $R_{3'''}$, $R_5$, $R_{5'}$, X, n and p are as defined in the description, is used for the preparation of a compound of Formula (I).

In another particular embodiment a compound of Formula (Ib) or (VII),

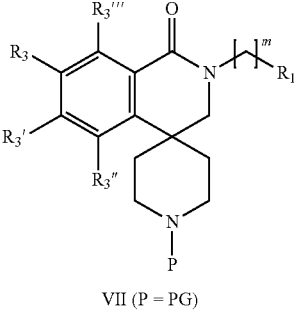

VII (P = PG)
Ib (P = Y)

wherein PG is a protecting group and Y is

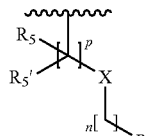

and wherein $R_1$, $R_2$, $R_3$, $R_{3'}$, $R_{3''}$, $R_{3'''}$, $R_5$, $R_{5'}$, X, m, n and p are as defined in the description, is used for the preparation of a compound of Formula (I).

In another particular embodiment a compound of Formula (Ic),

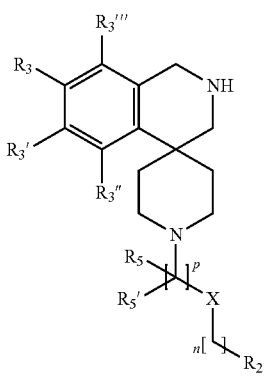

wherein $R_2$, $R_3$, $R_{3'}$, $R_{3''}$, $R_{3'''}$, $R_5$, $R_{5'}$, X, n and p are as defined in the description, is used for the preparation of a compound of Formula (I).

In another particular embodiment a compound of Formula (Id),

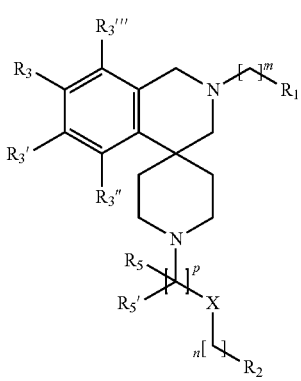

wherein $R_1$, $R_2$, $R_3$, $R_{3'}$, $R_{3''}$, $R_{3'''}$, $R_5$, $R_{5'}$, X, m, n and p are as defined in the description, is used for the preparation of a compound of Formula (I).

In another particular embodiment a compound of Formula (II),

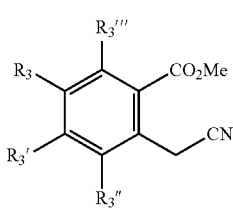

wherein $R_3$, $R_{3'}$, $R_{3''}$, $R_{3'''}$ are as defined in the description, is used for the preparation of a compound of Formula (I).

In another particular embodiment a compound of Formula (IIIa) or (IIIb),

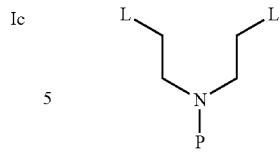

IIIa (P = PG)
IIIb (P = Y)

wherein PG is a protecting group and Y is

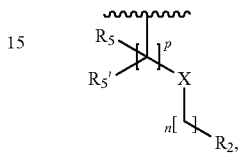

and wherein $R_2$, $R_5$, $R_{5'}$, X, n and p are as defined in the description, L is a leaving group such as chloro, bromo, mesylate or toxylate, is used for the preparation of a compound of Formula (I).

In another particular embodiment a compound of Formula (IVa) or (IVb),

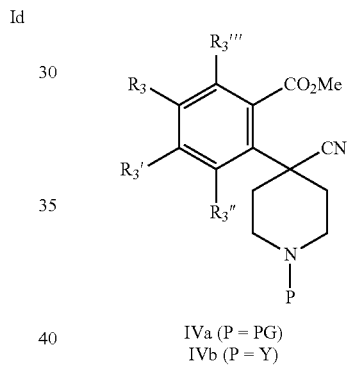

IVa (P = PG)
IVb (P = Y)

wherein PG is a protecting group and Y is

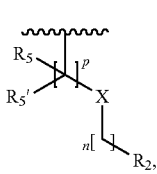

and wherein $R_2$, $R_3$, $R_{3'}$, $R_{3''}$, $R_{3'''}$, $R_5$, $R_{5'}$, X, n and p are as defined in the description, is used for the preparation of a compound of Formula (I).

In another particular embodiment a compound of Formula (VIa),

wherein $R_1$ and m are as defined in the description and L is a leaving group such as chloro, bromo, mesylate or toxylate, is used for the preparation of a compound of Formula (I).

In another particular embodiment a compound of Formula (VIb),

*(VIb)* — structure: aldehyde H-C(=O)-CH₂-[ ]ₘ₋₁-R₁ wherein R₁ and m are as defined in the description, is used for the preparation of a compound of Formula (I).

In another particular embodiment a compound of Formula (VIc),

*(VIc)* — structure: W-C(=O)-CH₂-[ ]ₘ₋₁-R₁ wherein R₁ and m are as defined in the description and W is chloro, bromo, —OH, OMe, or OEt, is used for the preparation of a compound of Formula (I).

In another particular embodiment a compound of Formula (VId),

*(VId)* — structure: (O-C(=O)-R₆)₂ (anhydride)

wherein R₆ is as defined in the description, is used for the preparation of a compound of Formula (I).

In another particular embodiment a compound of Formula (VIII),

*(VIII)* — spiro isoquinolinone-piperidine structure with substituents R₃, R₃', R₃'', R₃''' wherein R₃, R₃', R₃'', and R₃''' are as defined in the description, is used for the preparation of a compound of Formula (I).

In another particular embodiment a compound of Formula (IX),

*(IX)* — N-substituted spiro isoquinolinone-piperidine with R₁, R₃, R₃', R₃'', R₃''', and (CH₂)ₘ chain wherein R₁, R₃, R₃', R₃'', R₃''' and m are as defined in the description, is used for the preparation of a compound of Formula (I).

In another particular embodiment a compound of Formula (Xa) or (Xb),

*(Xa)* — structure with CHO, R₅, R₅', X, (CH₂)ₙ, R₂, p-1

*(Xb)* — structure with L, R₅, R₅', X, (CH₂)ₙ, R₂, p wherein R₂, R₅, R₅', X, n and p are as defined in the description and L is a leaving group such as chloro, bromo, mesylate or tosylate, is used for the preparation of a compound of Formula (I).

In another particular embodiment a compound of Formula (Ia') or (V'),

*(V'/Ia')* — spiro tetrahydroisoquinoline-piperidine with R₃, R₃', R₃'', R₃''', R₄, R₄', NH, and N-P V' (P = PG)
Ia' (P = Y)

wherein PG is a protecting group and Y is structure: R₅, R₅', X, (CH₂)ₙ, R₂, p wherein $R_2$, $R_3$, $R_{3'}$, $R_{3''}$, $R_{3'''}$, $R_4$, $R_{4'}$, $R_5$, $R_{5'}$, X, n and p are as defined in the description, is used for the preparation of a compound of Formula (I).

In another particular embodiment a compound of Formula (Ib') or (VII'),

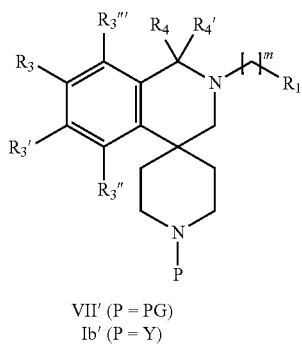

VII' (P = PG)
Ib' (P = Y)

wherein PG is a protecting group and Y is

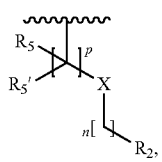

and wherein $R_1$, $R_2$, $R_3$, $R_{3'}$, $R_{3''}$, $R_{3'''}$, $R_4$, $R_{4'}$, $R_5$, $R_{5'}$, X, m, n and p are as defined in the description, is used for the preparation of a compound of Formula (I).

In another particular embodiment a compound of Formula (Ic')

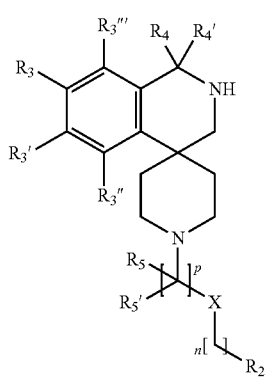

Ic' wherein $R_2$, $R_3$, $R_{3'}$, $R_{3''}$, $R_{3'''}$, $R_4$, $R_{4'}$, $R_5$, $R_{5'}$, X, n and p are as defined in the description, is used for the preparation of a compound of Formula (I).

In another particular embodiment a compound of Formula (Id'),

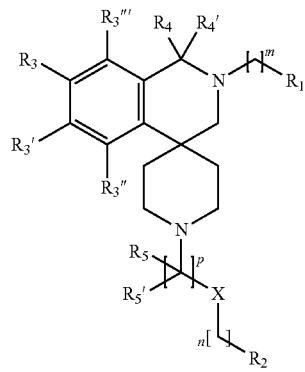

Id' wherein $R_1$, $R_2$, $R_3$, $R_{3'}$, $R_{3''}$, $R_{3'''}$, $R_4$, $R_{4'}$, $R_5$, $R_{5'}$, X, m, n and p are as defined in the description, is used for the preparation of a compound of Formula (I).

In another particular embodiment a compound of Formula (VIII'),

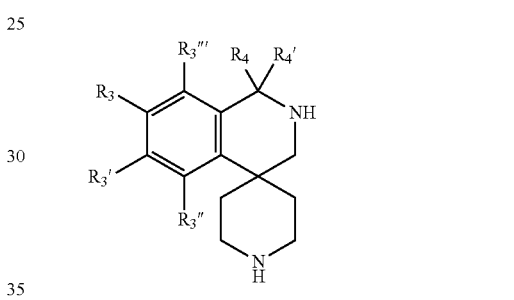

VIII' wherein $R_3$, $R_{3'}$, $R_{3''}$, $R_{3'''}$, $R_4$ and $R_{4'}$ are as defined in the description, is used for the preparation of a compound of Formula (I).

In another particular embodiment a compound of Formula (IX'),

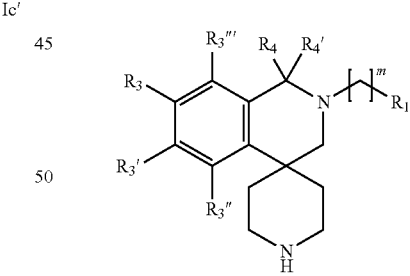

IX' wherein $R_1$, $R_3$, $R_{3'}$, $R_{3''}$, $R_{3'''}$, $R_4$, $R_{4'}$ and m are as defined in the description, is used for the preparation of a compound of Formula (I).

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formula I or a pharmaceutically acceptable salt or stereoisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrups or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formula I, or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis

A process is described in Scheme 1 for the preparation of compounds of general Formula (I), wherein p, m, n, $R_1$, $R_2$, $R_3$, $R_{3'}$, $R_{3''}$, $R_{3'''}$, $R_5$, $R_{5'}$, and X have the meanings defined above.

Scheme 1
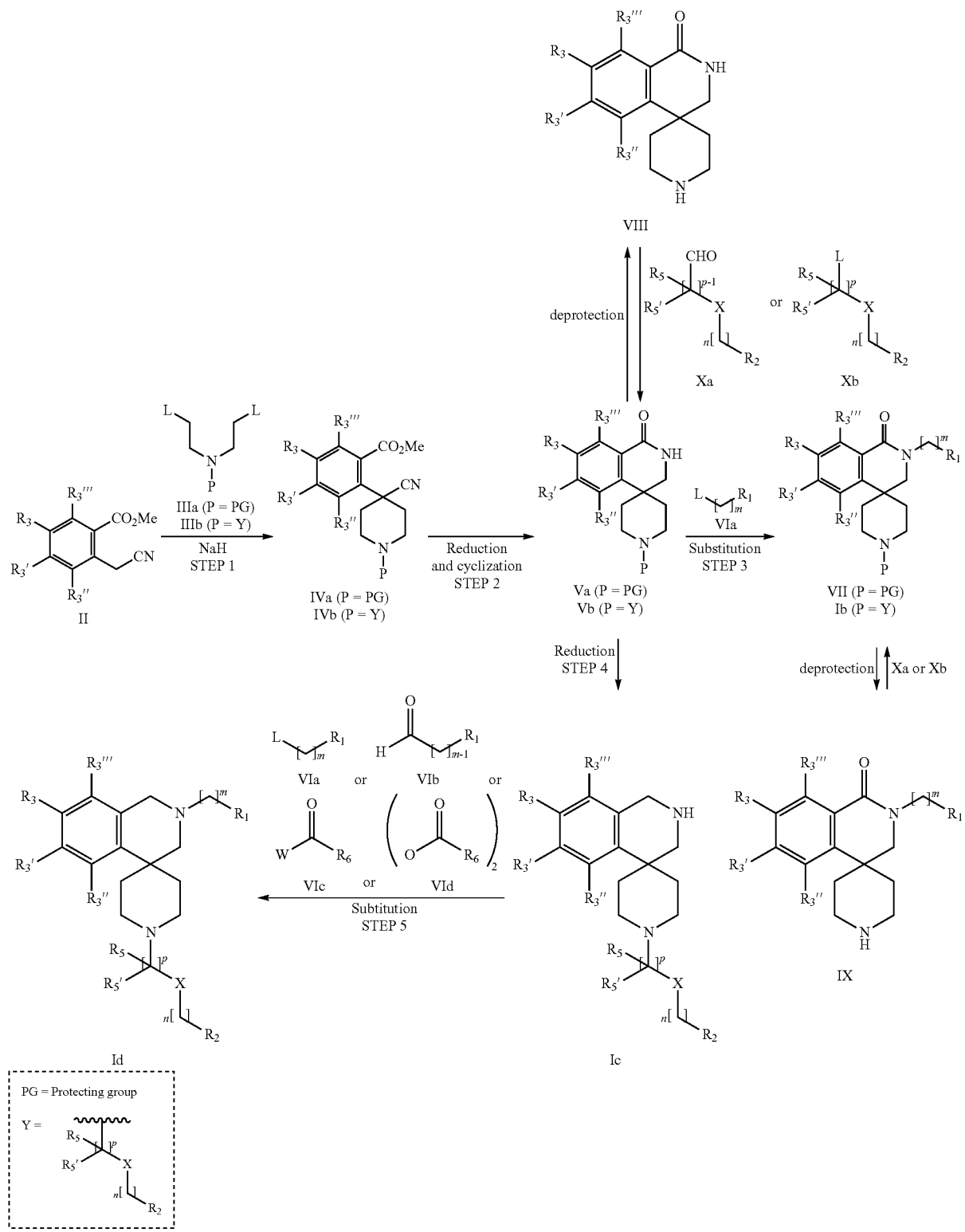
Where, L is a leaving group such as chloro, bromo, mesylate or toxylate and W is chloro, bromo, —OH, OMe or OEt, Y is the group indicated in Scheme 1 and PG is a protecting group.
This process is carried out as described below:
Step 1:
A compound of formula IVa or IVb is prepared by treating a compound of formula II with a strong base such as NaH in a suitable solvent such as DMF, at a suitable temperature comprised between 0° C. and room temperature, preferably at room temperature and subsequently treating the resulting deprotonated intermediate with a compound of formula IIIa of IIIb at a suitable temperature comprised between r.t. and 100° C., preferably at 100° C.

Step 2:

The reduction of nitrile in a compound of formula IVa or IVb and subsequent in situ cyclization of the generated intermediate amine compound renders a compound of general formula V or Ia. The reduction reaction can be carried out with hydrogen at a pressure comprised between 1 and 10 bar, preferably at 5 bars in a suitable solvent such as methanol or ethanol, in the presence of Raney nickel, at a suitable temperature comprised between room temperature and 50° C., preferably at room temperature. This reaction can be also effected in the presence of a reducing agent such as lithium aluminium hydride or diborane.

Step 3:

Compounds of general formula VII or Ib are prepared by N-alkylation of lactams of general formula V or Ia with a compound of formula VIa in a suitable solvent such as tetrahydrofuran, in the presence of a strong base such as NaH at a suitable temperature comprised between room temperature and the reflux temperature.

Step 4:

Compounds of general formula Ic are prepared by reduction of a lactam compound of formula Ia with a suitable agent such as aluminium hydride, in a suitable solvent such as tetrahydrofurane, at a suitable temperature comprised between room temperature and 60° C., preferably at 60° C. Aluminium hydride is freshly prepared before the reduction reaction by treating lithium aluminium hydride with aluminium trichloride.

Step 5:

Compounds of general formula Id are prepared by substitution of the NH group of compounds Ic, with appropriate methods. Thus the alkylation of Ic with a compound of formula VIa is carried out in a suitable solvent, such as acetonitrile, dichloromethane, 1,4-dioxane or dimethylformamide, in the presence of an inorganic base such as $K_2CO_3$ or $Cs_2CO_3$, or an organic base such as triethylamine or diisopropylethylamine, at a suitable temperature comprised between room temperature and the reflux temperature, preferably heating, or alternatively, the reactions can be carried out in a microwave reactor. Additionally, an activating agent such as NaI can be used.

The reductive amination of a compound of formula Ic with a compound of formula VIb, is carried out in the presence of a reductive reagent, preferably sodium triacetoxyborohydride, in a suitable solvent, preferably dichloromethane at a suitable temperature comprised between room temperature and the reflux temperature, preferably at room temperature.

The acylation reaction of a compound of formula Ic with a compound of formula VIc or VId can be effected in different conditions depending on the acid reagent nature. Preferably, VIc is an acid chloride and the reaction is carried out in the presence of a suitable solvent, such as acetonitrile, dichloromethane, 1,4-dioxane or dimethylformamide, preferably in dichloromethane; in the presence of an organic base such as triethylamine, diisopropylethylamine or pyridine, preferably diisopropylethylamine; at a suitable temperature comprised between room temperature and the reflux temperature, preferably at room temperature.

The process described by Steps 1 to 5 represents the general route for the preparation of compounds of formula I. Additionally, the functional groups present in any of the positions can be interconverted using reactions known to those skilled in the art.

Among these transformations, the protecting groups of the different intermediates can be deprotected at any step and subsequently substituted to provide variations in the group P. Thus, compounds V can be deprotected to provide compounds VIII and compounds VII to provide compounds IX. If the protecting group is benzyl, the deprotection is carried out with hydrogen at a pressure comprised between 1 and 10 bar, in a suitable solvent such as methanol or ethanol, optionally in the presence of an acid such as acetic or hydrochloric acid, at a suitable temperature comprised between room temperature and the reflux temperature, preferably at room temperature.

From deprotected compounds of general formula VIII or IX, compounds of general formula Ia or Ib can be respectively prepared by reaction with suitable reagents, such as those of formula Xa-b, using different conditions depending on the reagent nature. Thus:

The reductive amination with a compound of formula Xa, is carried out in the presence of a reductive reagent, preferably sodium triacetoxyborohydride, in a suitable solvent, preferably ethanol, at a suitable temperature comprised between room temperature and the reflux temperature, preferably at room temperature.

The alkylation reaction with a compound of formula Xb is carried out in a suitable solvent, such as acetonitrile, dichloromethane, 1,4-dioxane or dimethylformamide; in the presence of an inorganic base such as $K_2CO_3$ or $Cs_2CO_3$, or an organic base such as triethylamine or diisopropylethylamine; at a suitable temperature comprised between room temperature and the reflux temperature, preferably heating, or alternatively, this reaction can be carried out in a microwave reactor. Additionally, an activating agent such as NaI can be used.

Additionally, compounds I in which $R_4$ or $R_{4'}$ are different from H can be obtained by electrophilic halogenation of the benzylic position of compounds Id using for example an N-halosuccinimide in an apolar solvent such as carbon tetrachloride at any temperature between room temperature and that of the solvent reflux, followed by nucleophilic substitution with a suitable derivative, such as an organometallic reagent, in the presence of a suitable solvent, such as tetrahydrofuran at a suitable temperature, from −80° C. to that of the reflux of the solvent.

Examples

Intermediates and Examples

The following abbreviations are used in the examples:
ACN: acetonitrile
AcOH: acetic acid
Anh: anhydrous
DCM: dichloromethane
DIPEA: diisopropylethylamine
DMF: dimethylformamide
EtOH: ethanol
EX: example
h: hour/s
HPLC: high performance liquid chromatography
MeOH: methanol
MS: mass spectrometry
Min.: minutes
Ret.: retention time
r.t.: room temperature Sat: saturated
THF: tetrahydrofuran
y: yield The following methods were used to determine the HPLC-MS spectra:

A: Column Waters XSelect C18, 30×2.1 mm, 3.5μ; flow rate: 1 mL/min; A: ACN:10 mM Ammoniumbicarbonate in water (95:5); B: 10 mM Ammoniumbicarbonate in water; gradient: 2% to 98% A in 1.6 min, 1.4 min in 98% A.

B: Column Waters XSelect (C18, 30×2 mm, 3.5μ; flow rate: 1 mL/min; A: 0.1% formic acid in ACN; B: 0.1% formic acid in water; gradient: 2% to 98% A in 1.6 min, 1.4 min in 98% A.

C: Column Waters XSelect C18, 30×2.1 mm, 3.5μ; flow rate: 0.8 mL/min; A: 250 mM $NH_3$ in ACN; B: 250 mM $NH_3$ in water; gradient: 2% to 98% A in 3.5 min, 2.5 min in 98% A.

Intermediate 1.
N-benzyl-2-chloro-N-(2-chloroethyl)ethanamine

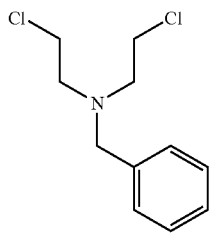 [SMILES: ClCCN(CCCl)Cc1ccccc1]

Triethylamine (5.06 g, 50.0 mmol, 6.95 mL) and benzaldehyde (7.96 g, 75 mmol, 7.63 mL) were added to a solution of bis(2-chloroethyl)amine hydrochloride (8.92 g, 50 mmol) in anh. DCM (200 mL). The suspension was stirred at r.t. for 30 min and then, sodium triacetoxyhydroborate (21.19 g, 100 mmol) was added portionwise giving a turbid solution that slightly warmed up for about 1-1.5 hours in an exothermic reaction. The mixture was stirred overnight at r.t and then diluted with DCM and carefully quenched with aqueous sodium bicarbonate. The aqueous phase was extracted with DCM, and the combined organic layers were dried over anh. $Na_2SO_4$, filtered and concentrated. The crude residue was purified by flash chromatography on $SiO_2$ (DCM), to afford the title compound as a colourless oil (9.18 g, y 77%).

HPLC-MS (Method A): Ret, 2.45 min; $ESI^+$-MS m/z, 232.1 (M+1).

Intermediate 2. Methyl 2-(1-benzyl-4-cyanopiperidin-4-yl)benzoate

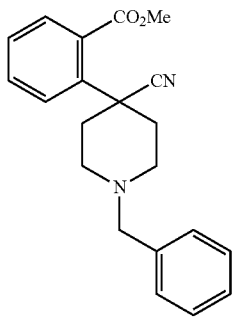 [SMILES: COC(=O)c1ccccc1C1(C#N)CCN(Cc2ccccc2)CC1]

To a suspension of sodium hydride (4.39 g, 110 mmol, 60%) in anh.DMF (200 mL), methyl 2-(cyanomethyl)benzoate (6.41 g, 36.6 mmol) was added portionwise and the mixture was stirred at r.t. for 30 min. Then, a solution of N-benzyl-2-chloro-N-(2-chloroethyl)ethanamine (intermediate 1, 9.20 g, 38.4 mmol) in anh. DMF (100 mL) was dripped in and the reaction mixture was stirred at 100° C. for 2 h. The reaction was quenched with ice and extracted with ethyl acetate. The combined organic layers were washed with brine, dried over anh. $Na_2SO_4$, filtered and evaporated to dryness to obtain a crude residue that was purified by flash chromatography on $SiO_2$ (5→100% ethyl acetate/heptane), to give the title compound as a light brown oil (4.85 g, y 35%).

HPLC-MS (Method A): Ret, 2.34 min; ESI+-MS m/z, 335.1 (M+1).

Example 1. 1'-Benzyl-2,3-dihydro-1H-spiro[isoquinoline-4,4'-piperidin]-1-one

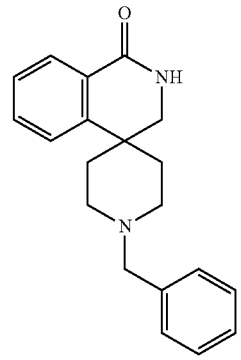 [SMILES: O=C1NCC2(CCN(Cc3ccccc3)CC2)c2ccccc21]

Raney nickel (3.70 g, 21.59 mmol, 50%, circa 2.5 mL of slurry in water) and $NH_3$ (7 N in MeOH, 30 mL) were added to a solution of methyl 2-(1-benzyl-4-cyanopiperidin-4-yl)benzoate (4.83 g, 12.7 mmol) in MeOH (120 mL) in a glass autoclave, which was pressurised with 5 bar of hydrogen and the mixture heated at 50° C. overnight. This hydrogenation cycle was repeated 3 times adding fresh catalyst each time until reaction completion. Finally, the solids were filtered off and the solvent was removed under vacuum. The crude compound was purified by flash chromatography on $SiO_2$ (0→10% MeOH/DCM), to give the title compound as an off-white foam (2.5 g, y 57%).

HPLC-MS (Method B): Ret, 1.52 min; ESI+-MS m/z, 307.2 (M+1).

Example 2. 1'-Benzyl-2-methyl-2,3-dihydro-1H-spiro[isoquinoline-4,4'-piperidin]-1-one

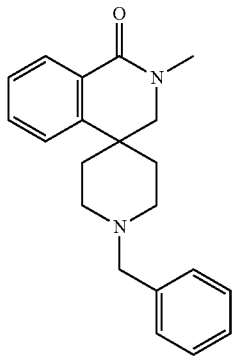 [SMILES: CN1CC2(CCN(Cc3ccccc3)CC2)c2ccccc2C1=O]

To a solution of 1'-benzyl-2,3-dihydro-1H-spiroisoquinoline-4,4'-piperidin]-1-one (example 1, 61 mg, 0.2 mmol) in THF (4 mL) under nitrogen atmosphere, sodium hydride (8.80 mg, 0.220 mmol, 60% in mineral oil) was added. After 15 min, iodomethane (34 mg, 0.240 mmol, 0.015 mL) was added and the mixture was stirred at r.t. for 60 h. The mixture was quenched with a few drops of water and it was evaporated to dryness. The crude residue was purified by flash chromatography on SiO$_2$ (0→5% MeOH/DCM), to afford the title compound as a solid (58 mg, y 86%).

HPLC-MS (Method A): Ret, 2.2 min; ESI+-MS m/z, 321.2 (M+1).

Example 3. 1'-Benzyl-2-ethyl-2,3-dihydro-1H-spiro[isoquinoline-4,4'-piperidin]-1-one

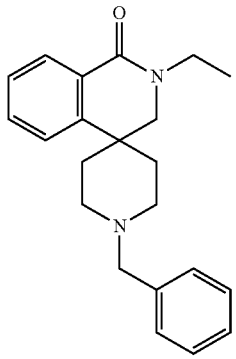 [SMILES: CCN1CC2(CCN(Cc3ccccc3)CC2)c2ccccc2C1=O]

1'-Benzyl-2,3-dihydro-1H-spiro[isoquinoline-4,4'-piperidin]-1-one (example 1, 61 mg, 0.2 mmol) was dissolved in anh. THF (2 mL) under a nitrogen atmosphere and solid sodium hydride (9.60 mg, 0.24 mmol, 60% in mineral oil) was added in one portion. After 15 min, iodoethane (41 mg, 0.26 mmol) was added to the white suspension. After 5 h of reflux, the mixture was cooled down, quenched with 0.5 mL water and evaporated to dryness. The crude residue was purified by flash chromatography on SiO$_2$ (0→10% MeOH/DCM), to give the title compound as a colourless oil (64 mg, y 93%).

HPLC-MS (Method A): Ret, 2.26 min; ESI+-MS m/z, 335.2 (M+1).

Example 4. 1'-Phenethyl-2,3-dihydro-1H-spiro[isoquinoline-4,4'-piperidin]-1-one

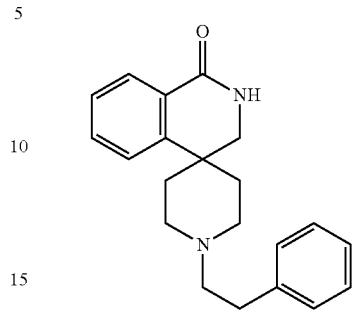

a) 2,3-Dihydro-1H-spiro[isoquinoline-4,4'-piperidin]-1-one

1'-Benzyl-2,3-dihydro-1H-spiro[isoquinoline-4,4'-piperidin]-1-one (0.919 g, 3 mmol) was dissolved in a mixture of MeOH (15 mL) and ethyl acetate (15 mL) and subjected to hydrogenolysis at 1 bar of hydrogen in the presence of palladium on carbon (0.639 g, 0.6 mmol, 10%). The mixture was refluxed overnight and then cooled down and filtered through celite rinsing with MeOH and ethyl acetate. The filtrate was concentrated to dryness to afford 2,3-dihydro-1H-spiro[isoquinoline-4,4'-piperidin]-1-one as a white solid (623 mg, y 90%).

HPLC-MS (Method A): Ret, 1.67 min; ESI+-MS m/z, 217.1 (M+1).

b) Title Compound 2,3-Dihydro-1H-spiro[isoquinoline-4,4'-piperidin]-1-one (obtained in step a, 222 mg, 1.02 mmol) was suspended in EtOH (15 mL) and phenylacetaldehyde (334 μL, 2.57 mmol) was added followed by some drops of AcOH. The solution was stirred for 2 h at r.t. and sodium triacetoxyborohydride (1.08 g, 5.13 mmol) was added. The reaction mixture was stirred at r.t. overnight and then it was quenched with H$_2$O and partially concentrated to remove most of the EtOH. The residue was separated between DCM and sat. aqueous NaHCO$_3$ solution. The aqueous layer was further extracted with DCM and be combined organic layers were dried over anh. Na$_2$SO$_4$, filtered and evaporated to dryness. The crude residue was purified by flash chromatography on SiO$_2$ (0→10% MeOH/DCM), to give the title compound as a yellow oil (231 mg, yield 70%).

HPLC-MS (Method A): Ret, 2.16 min; ESI+-MS m/z, 321.2 (M+1).

Example 5. 2-Methyl-1'-phenethyl-2,3-dihydro-1H-spiro[isoquinoline-4,4'-piperidin]-1-one

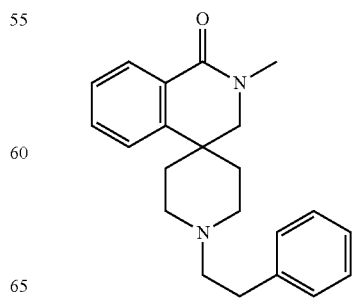

Following a similar procedure to that described in example 3, but starting from the compound obtained in example 4, the title compound was obtained as a yellow solid.

HPLC-MS (Method A): Ret, 2.19 min; ESI⁺-MS m/z, 335.2 (M+1).

Example 6. 2-ethyl-1'-phenethyl-2,3-dihydro-1H-spiro[isoquinoline-4,4'-piperidin]-1-one The method of example 3 was used for the preparation of example 6 using example 4 as a starting material:

| EX | Structure | Chemical name | Method | Ret (min) | MS (M + H) |
|---|---|---|---|---|---|
| 6 | 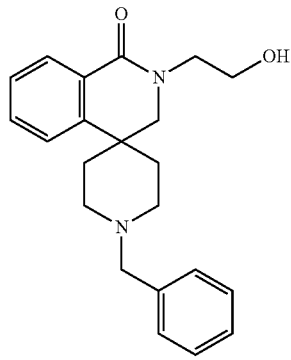 [SMILES: O=C1c2ccccc2C2(CCN(Cc3ccccc3)CC2)CN1CCO] | 2-ethyl-1'-phenethyl-2,3-dihydro-1H-spiro[iso-quinoline-4,4'-piperidin]-1-one | A | 2.25 | 349.2 |

Example 7. 1'-Benzyl-2-(2-hydroxyethyl)-2,3-dihydro-1H-spiro[isoquinoline-4,4'-piperidin]-1-one a) Ethyl 2-(1'-benzyl-1-oxo-1H-spiro[isoquinoline-4,4'-piperidine]-2(3H)-yl)acetate Sodium hydride (8.80 mg, 0.22 mmol, 60% in mineral oil) was added to a solution of 1'-benzyl-2,3-dihydro-1H-spiro[isoquinoline-4,4'-piperidin]-1-one (example 1, 61 mg, 0.2 mmol) in anh. THF (2 mL). After 15 min ethyl 2-bromoacetate (40 mg, 0.24 mmol) was added and the suspension was stirred at r.t. for 1 h. The mixture was quenched with a few drops of water and evaporated to dryness. The crude residue was purified by flash chromatography on SiO₂ (0→4% MeOH/DCM), to give the title compound as a colourless oil (75 mg, y 95%).

HPLC-MS (Method A): Ret, 2.27 min; ESI+-MS m/z, 393.2 (M+1).

b) Title Compound

Ethyl 2-(1'-benzyl-1-oxo-1H-spiro[isoquinoline-4,4'-piperidine]-2(3H)-yl)acetate (obtained in step a, 75 mg, 0.19 mmol) was dissolved in anh. THF (5 mL) under a nitrogen atmosphere and treated with lithium tetrahydroborate (THF solution, 0.38 mmol, 0.19 mL). The mixture was stirred at r.t. for 2 h and then additional lithium tetrahydroborate (0.380 mmol, 0.19 mL) was added and the mixture was allowed to stir at r.t. overnight. The mixture was quenched with 1 N HCl and then alkalised with aqueous sodium carbonate and extracted with DCM. The combined organic layers were dried over Na₂SO₄, filtered and evaporated to dryness. The crude residue was purified by flash chromatography on SiO₂ (0→6% MeOH/DCM), to afford the title compound as a white solid (19 mg, y 28%).

HPLC-MS (Method A): Ret, 2.07 min; ESI+-MS m/z, 351.2 (M+1).

Example 8. 1'-Phenethyl-2,3-dihydro-1H-spiro[isoquinoline-4,4'-piperidine]

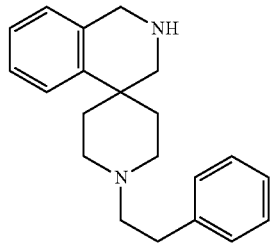 [SMILES: c1ccc(CCN2CCC3(CC2)CNCc2ccccc23)cc1]

Aluminum chloride (81 mg, 0.61 mmol) was cooled in an ice-bath and anh. diethyl ester (2.5 mL) was added slowly. After 10 min. anh. THF (1.5 mL) was added followed by LiAlH₄ (2.4 M in THF, 780 µL, 1.87 mmol). The reaction mixture was stirred for 30 min at r.t. Then a suspension of 1'-phenethyl-2,3-dihydro-1H-spiro[isoquinoline-4,4'-piperidin]-1-one (example 4, 150 mg, 0.47 mmol) in THF (2.5 mL) was added and the cooling bath was removed. The reaction mixture was stirred at 60° C. for 3 h and then it was quenched with 1 N HCl until pH-2. The suspension was basified with with sat. NaHCO₃ solution and partially concentrated to remove most of the diethyl ether and THF. The residue was extracted with DCM and the combined organic layers were dried over anh. Na₂SO₄, filtered and evaporated to dryness. The crude residue was purified by flash chromatography on SiO₂ (from DCM to 5% 7N NH₃/MeOH in DCM), to give the title compound as an oil (96 mg, y 67%).

HPLC-MS (Method C): Ret, 3.51 min; ESI+-MS m/z, 307.3 (M+1).

Example 9. 2-Methyl-1'-phenethyl-2,3-dihydro-1H-spiro[isoquinoline-4,4'-piperidine]

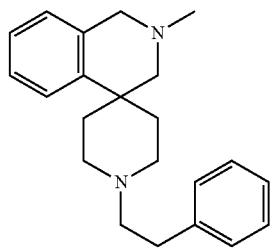 [SMILES: CN1Cc2ccccc2C2(CCN(CCc3ccccc3)CC2)C1]

Formaldehyde (37% solution in H₂O, 23 µL, 0.31 mmol) and sodium triacetoxy borohydride (66.2 mg, 0.31 mmol) were added to a solution of 1'-phenethyl-2,3-dihydro-1H-spiro[isoquinoline-4,4'-piperidine] (example 8, 31.9 mg, 0.1 mmol) in DCM (2 mL) and the reaction mixture was stirred at r.t. for 1 h. The mixture was quenched with sat. aqueous NaHCO₃ solution and the layers were separated. The aqueous layer was extracted with DCM and the combined organic layers were dried over anh. Na₂SO₄, filtered and evaporated to dryness. The crude residue was purified by flash chromatography on SiO₂ (0→10% MeOH/DCM), to give the title compound as a white solid (33 mg, y 76%).

HPLC-MS (Method A): Ret, 2.43 min; ESI+-MS m/z, 321.3 (M+1).

Example 10. 1-(1'-Phenethyl-1H-spiro[isoquinoline-4,4'-piperidine]-2(3H)-yl)ethanone

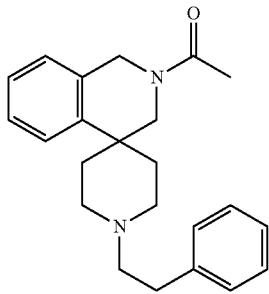 [SMILES: CC(=O)N1Cc2ccccc2C2(CCN(CCc3ccccc3)CC2)C1]

DIPEA (24 µL, 0.135 mmol) and acetyl chloride (8.1 µL, 0.11 mL) were added to a solution of 1'-phenethyl-2,3-dihydro-1H-spiro[isoquinoline-4,4'-piperidine] (example 8, 31.9 mg, 0.1 mmol) in anh. DCM (2 mL) and the mixture was stirred at r.t. for 1 h. The reaction mixture was concentrated to dryness and the crude residue was purified by flash chromatography on SiO₂ (0→10% MeOH/DCM), to afford the title compound as a white solid (28 mg, y 76%).

HPLC-MS (Method A): Ret, 2.23 min; ESI+-MS m/z, 349.2 (M+1).

Example 11. 2-(2-Hydroxyethyl)-1'-phenethyl-2,3-dihydro-1H-spiro[isoquinoline-4,4'-piperidin]-1-one

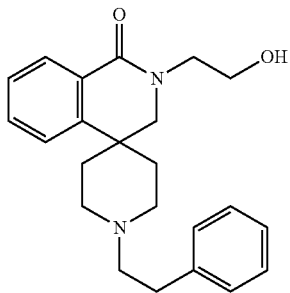 [SMILES: O=C1c2ccccc2C2(CCN(CCc3ccccc3)CC2)CN1CCO]

a) 1'-Phenethyl-2-(2-(tetrahydro-2H-pyran-2-yloxy)ethyl)-2,3-dihydro-1H-spiro[isoquinoline-4,4'-piperidin]-1-one NaH (60% in mineral oil, 34.6 mg, 0.87 mmol) was added to a suspension of 1'-phenethyl-2,3-dihydro-1H-spiro[isoquinoline-4,4'-piperidin]-1-one (example 4, 231 mg, 0.721 mmol) in anh. THF (10 mL) and the mixture was stirred for 25 min at r.t. Then, 2-(2-bromoethoxy) tetrahydro-2H-pyran (131 µL, 0.87 mmol) was added and the reaction mixture was stirred at 50° C. overnight. Fresh portions of NaH (60% in mineral oil, 7.2 mg, 0.18 mmol) and 2-(2-bromoethoxy) tetrahydro-2H-pyran (27 µL, 0.18 mmol) were added, followed by NaI (11 mg, 0.07 mmol) and the reaction mixture was refluxed overnight. Then, it was cooled down to r.t., quenched with a few drops of H₂O and concentrated to dryness. The crude residue was purified by flash chromatography on SiO₂ (0→10% MeOH/DCM), to yield 1'-phenethyl-2-(2-((tetrahydro-2H-pyran-2-yl)oxy)ethyl)-2,3-dihydro-1H-spiro[isoquinoline-4,4'-piperidin]-1-one as a colourless oil (92 mg, y 28%).

HPLC-MS (Method A): Ret, 2.34 min; ESI+-MS m/z, 449.3 (M+1).

b) Title Compound
1'-Phenethyl-2-(2-((tetrahydro-2H-pyran-2-yl)oxy)ethyl)-2,3-dihydro-1H-spiro[isoquinoline-4,4'-piperidin]-1-one (obtained in step a, 90 mg, 0.2 mmol) was dissolved in methanol (2 mL) and it was treated with an excess of HCl in 2-propanol (4 mmol, 0.8 mL). The reaction mixture was stirred at r.t. for 3 h and then the solvents were evaporated to dryness. The residue was freeze-dried from water/ACN overnight to afford the title compound as a pale yellow solid (84 mg, y 99%).

HPLC-MS (Method A): Ret, 2.07 min; ESI+-MS m/z, 365.2 (M+1).

Table of Examples with binding to the µ-Opioid Receptor and the σ1-Receptor:
Biological Activity
Pharmacological Study
Human σ₁ Receptor Radioligand Assay
To investigate binding properties of test compounds to human σ₁ receptor, transfected HEK-293 membranes and [³H](+)-pentazocine (Perkin Elmer, NET-1056), as the radioligand, were used. The assay was carried out with 7 µg of membrane suspension, 5 nM of [³H](+)-pentazocine in either absence or presence of either buffer or 10 µM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail Human µ-Opioid Receptor Radioligand Assay
To investigate binding properties of test compounds to human µ-opioid receptor, transfected CHO-K1 cell membranes and [³H]-DAMGO (Perkin Elmer, ES-542-C), as the radioligand, were used. The assay was carried out with 20 µg of membrane suspension, 1 nM of [³H]-DAMGO in either absence or presence of either buffer or 10 µM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:
As this invention is aimed at providing a compound or a chemically related series of compounds which act as dual ligands of the σ₁ receptor and the µ-opioid receptor it is a very preferred embodiment in which the compounds are selected which act as dual ligands of the σ₁ receptor and the µ-opiod receptor and especially compounds which have a binding expressed as $K_i$ which is preferably <1000 nM for both receptors, more preferably <500 nM, even more preferably <100 nM.

The following scale as been adopted for representing the binding to the the $\sigma_1$ receptor and the µ-opiod receptor expressed as $K_i$:

+ Both $K_i$-µ and $K_i$-$\sigma_1$ >500 nM
++ One $K_i$<500 nM while the other $K_i$ is >=500 nM
+++ Both $K_i$-µ and $K_i$-$\sigma_1$ <500 nM
++++ Both $K_i$-µ and $K_i$-$\sigma_1$ <100 nM All compounds prepared in the present application exhibit binding to the $\sigma_1$ receptor and the µ-opiod receptor, in particular the following binding results are shown:

| EX | µ and $\sigma_1$ dual |
|---|---|
| 1 | ++ |
| 2 | ++ |
| 3 | ++ |
| 4 | +++ |
| 5 | +++ |
| 6 | +++ |
| 7 | ++ |
| 8 | +++ |
| 9 | +++ |
| 10 | ++ |
| 11 | ++ |

The invention claimed is:

1. A compound of general formula (I):

(I)

wherein
m is 0, 1, 2, 3, 4, 5 or 6;
n is 0, 1, 2, 3 or 4;
p is 1, 2 or 3;
$R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —C(O)$R_6$, —C(O)O$R_6$, —C(O)N$R_6R_{6'}$ and —S(O)$_2R_6$;
  wherein $R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
    wherein the alkyl, alkenyl or alkynyl in $R_1$ or $R_6$, if substituted, is substituted with one or more substituent/s selected from —OR$_{11}$, halogen, —CN, haloalkyl, haloalkoxy, —SR$_{11}$, —S(O)R$_{11}$, and —S(O)$_2R_{11}$;

wherein $R_{11}$ is selected from hydrogen, unsubstituted $C_{1-6}$ alkyl, unsubstituted $C_{2-6}$ alkenyl, unsubstituted $C_{2-6}$ alkynyl;
$R_2$ is selected from substituted or unsubstituted monocyclic $C_{3-7}$ cycloalkyl, substituted or unsubstituted monocyclic aryl and substituted or unsubstituted monocyclic heterocyclyl;
  wherein said cycloalkyl, aryl or heterocyclyl in $R_2$, if substituted, is substituted with one or more substituent/s selected from halogen, —R$_{12}$, —OR$_{12}$, —NO$_2$, —NR$_{12}R_{12'''}$, NR$_{12}$C(O)R$_{12'}$, —NR$_{12}$S(O)$_2R_{12'}$, —S(O)$_2$NR$_{12}R_{12'}$, —NR$_{12}$C(O)NR$_{12'}R_{12''}$, —SR$_{12}$, —S(O)R$_{12}$, S(O)$_2R_{12}$, —CN, haloalkyl, haloalkoxy, —C(O)OR$_{12}$, —C(O)NR$_{12}R_{12'}$, and —NR$_{12}$S(O)$_2$NR$_{12}R_{12'''}$;
  wherein the cycloalkyl or non-aromatic heterocyclyl in $R_2$, if substituted, can also be substituted with

▽ or =O;
    wherein $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl;
    and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;
X is selected from a bond, —C(R$_xR_{x'}$)—, and —C(R$_x$)(OR$_7$)—;
  $R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_7$, —C(O)NR$_7R_{7'}$, —NR$_7$C(O)R$_7$, and —NR$_7R_{7''}$;
  $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
  $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;
  and wherein $R_{7'''}$ is selected from hydrogen, unsubstituted $C_{1-6}$ alkyl, unsubstituted $C_{2-6}$ alkenyl, unsubstituted $C_{2-6}$ alkynyl and -Boc;
$R_3$ is selected from hydrogen, halogen, —R$_9$, —OR$_9$, —NO$_2$, —NR$_9R_{9'''}$, —NR$_9$C(O)R$_{9'}$, —NR$_9$C(O)OR$_{9'}$, —NR$_9$S(O)$_2R_{9'}$, —S(O)$_2$NR$_9R_{9'}$, —NR$_9$C(O)NR$_9R_{9'''}$, —SR$_9$, —S(O)R$_9$, —S(O)$_2R_9$, —CN, haloalkyl, haloalkoxy, —C(O)OR$_9$, —C(O)NR$_9R_{9'}$, —NR$_9$S(O)$_2$NR$_9R_{9''}$ and —OC(O)R$_9$;
$R_{3'}$, $R_{3''}$ and $R_{3'''}$ are independently selected from hydrogen, halogen, —R$_9$, —OR$_9$, —NO$_2$, —NR$_9R_{9'''}$, —NR$_9$C(O)R$_{9'}$, —NR$_9$C(O)OR$_{9'}$, —NR$_9$S(O)$_2R_{9'}$, —S(O)$_2$NR$_9R_{9'}$, —NR$_9$C(O)NR$_9R_{9'''}$, —SR$_9$, —S(O)R$_9$, —S(O)$_2R_9$, —CN, haloalkyl, haloalkoxy, —C(O)OR$_9$, —C(O)NR$_9R_{9'}$, —NR$_9$S(O)$_2$NR$_9R_{9''}$ and —OC(O)R$_9$;
  wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;
  and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

R$_4$ is selected from hydrogen, substituted or unsubstituted C$_{1-6}$ alkyl, substituted or unsubstituted C$_{2-6}$ alkenyl, substituted or unsubstituted C$_{2-6}$ alkynyl, —C(O)OR$_8$, —C(O)NR$_8$R$_{8'}$, R$_{4'}$ is selected from hydrogen, or substituted or unsubstituted C$_{1-6}$ alkyl, substituted or unsubstituted C$_{2-6}$ alkenyl, and substituted or unsubstituted C$_{2-6}$ alkynyl;
  wherein R$_8$, R$_{8'}$ and R$_{8''}$ are independently selected from hydrogen, unsubstituted C$_{1-6}$ alkyl, unsubstituted C$_{2-6}$ alkenyl, and unsubstituted C$_{2-6}$ alkynyl;
  and wherein R$_{8'''}$ is selected from hydrogen, unsubstituted C$_{1-6}$ alkyl, unsubstituted C$_{2-6}$ alkenyl, unsubstituted C$_{2-6}$ alkynyl and -Boc;
or R$_4$ and R$_{4'}$, together with the carbon to which they are attached, form a C=O group;

R$_5$ and R$_{5'}$ are independently selected from hydrogen, or substituted or unsubstituted C$_{1-6}$ alkyl, substituted or unsubstituted C$_{2-6}$ alkenyl, and substituted or unsubstituted C$_{2-6}$ alkynyl;

the alkyl, alkenyl or alkynyl, other than those defined in R$_1$, R$_2$ or R$_6$, if substituted, is substituted with one or more substituent/s selected from —OR$_{10}$, halogen, —CN, haloalkyl, haloalkoxy, —SR$_{10}$, —S(O)R$_{10}$, and —S(O)$_2$R$_{10}$;
  wherein R$_{10}$ and R$_{10'}$ are independently selected from hydrogen, unsubstituted C$_{1-6}$ alkyl, unsubstituted C$_{2-6}$ alkenyl, and unsubstituted C$_{2-6}$ alkynyl;

optionally as a stereoisomer, a racemate or a mixture of at least two stereoisomers, in any mixing ratio, or a corresponding salt thereof, or a corresponding solvate thereof;
with the proviso that:
  when —[CH$_2$]$_m$—R$_1$ is —C(O)R$_6$, —C(O)OR$_6$, —C(O)NR$_6$R$_{6'}$ or —S(O)$_2$R$_6$,
  and R$_4$ and R$_{4'}$ are both hydrogen,
  then —[CR$_5$R$_{5'}$]$_p$—X—[CH$_2$]$_n$ is not —CH$_2$—
and wherein the following compound is further excluded:

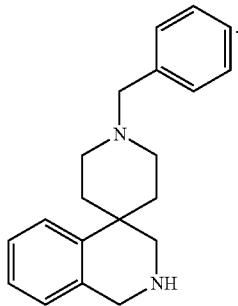 [SMILES: c1ccc(CN2CCC3(CC2)CNCc2ccccc23)cc1]

2. The compound according to claim 1, wherein
m is 0, 1, 2 and/or n is 0, 1 and/or p is 1.

3. The compound according to claim 1, wherein
R$_1$ is selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, substituted or unsubstituted heterocyclyl and —C(O)R$_6$, and wherein
  R$_6$ and R$_{6'}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl.

4. The compound according to claim 3, wherein R$_1$ is substituted or unsubstituted methyl.

5. The compound according to claim 3, wherein R$_6$ and R$_{6'}$ are independently selected from hydrogen, substituted or unsubstituted methyl, substituted or unsubstituted C$_{2-6}$ alkenyl and substituted or unsubstituted C$_{2-6}$ alkynyl.

6. The compound according to claim 1, wherein R$_2$ is substituted or unsubstituted monocyclic aryl.

7. The compound according to claim 6, wherein R$_2$ is substituted or unsubstituted phenyl.

8. The compound according to claim 1, wherein
X is selected from a bond and —C(R$_x$R$_{x'}$)—; and wherein
  R$_x$ is selected from hydrogen, substituted or unsubstituted C$_{1-6}$ alkyl, substituted or unsubstituted C$_{2-6}$ alkenyl, substituted or unsubstituted C$_{2-6}$ alkynyl; and
  R$_{x'}$ is selected from hydrogen, substituted or unsubstituted C$_{1-6}$ alkyl, substituted or unsubstituted C$_{2-6}$ alkenyl and substituted or unsubstituted C$_{2-6}$ alkynyl.

9. The compound according to claim 1, wherein
X is a bond.

10. The compound according to claim 1, wherein
R$_3$, R$_{3'}$, R$_{3''}$ and R$_{3'''}$ are independently selected from hydrogen, halogen, —R$_9$, —OR$_9$ and —NR$_9$R$_{9'''}$, and wherein
  R$_9$, R$_{9'}$ and R$_{9''}$ are independently selected from hydrogen, unsubstituted C$_{1-6}$ alkyl, unsubstituted C$_{2-6}$ alkenyl, and unsubstituted C$_{2-6}$ alkynyl;
  and wherein R$_{9'''}$ is selected from hydrogen, unsubstituted C$_{1-6}$ alkyl, unsubstituted C$_{2-6}$ alkenyl, unsubstituted C$_{2-6}$ alkynyl and -Boc.

11. The compound according to claim 1, wherein
R$_4$ is selected from hydrogen, substituted or unsubstituted C$_{1-6}$ alkyl, substituted or unsubstituted C$_{2-6}$ alkenyl and substituted or unsubstituted C$_{2-6}$ alkynyl; and
R$_{4'}$ is selected from hydrogen, or substituted or unsubstituted C$_{1-6}$ alkyl, substituted or unsubstituted C$_{2-6}$ alkenyl, and substituted or unsubstituted C$_{2-6}$ alkynyl; or
R$_4$ and R$_{4'}$ may form together with the carbon to which they are attached, a C=O group.

12. The compound according to claim 1, wherein
m is 0, 1 or 2;
n is 0 or 1;
p is 1;
R$_1$ is selected from hydrogen, substituted or unsubstituted C$_{1-6}$ alkyl, and —C(O)R$_6$, wherein R$_6$ is substituted or unsubstituted C$_{1-6}$ alkyl;
R$_2$ is substituted or unsubstituted monocyclic aryl;
X is a bond;
R$_3$, R$_{3'}$, R$_{3''}$ and R$_{3'''}$ are all hydrogen;
R$_4$ and R$_{4'}$ are both hydrogen, or R$_4$ and R$_{4'}$ may form together with the carbon to which they are attached, a C=O group; and
R$_5$ and R$_{5'}$ are both hydrogen.

13. The compound according to claim 12, wherein R$_1$ is substituted or unsubstituted methyl or —C(O)R$_6$, wherein R$_6$ is substituted or unsubstituted methyl.

14. The compound according to claim 12, wherein R$_2$ is substituted or unsubstituted phenyl.

15. The compound according to claim 1, wherein the compound is selected from:
1'-benzyl-2,3-dihydro-1H-spiro[isoquinoline-4,4'-piperidin]-1-one
1'-benzyl-2-methyl-2,3-dihydro-1H-spiro[isoquinoline-4,4'-piperidin]-1-one
1'-benzyl-2-ethyl-2,3-dihydro-1H-spiro[isoquinoline-4,4'-piperidin]-1-one
1'-phenethyl-2,3-dihydro-1H-spiro[isoquinoline-4,4'-piperidin]-1-one 2-methyl-1'-phenethyl-2,3-dihydro-1H-spiro[isoquinoline-4,4'-piperidin]-1-one
2-ethyl-1'-phenethyl-2,3-dihydro-1H-spiro[isoquinoline-4,4'-piperidin]-1-one
1'-benzyl-2-(2-hydroxyethyl)-2,3-dihydro-1H-spiro[isoquinoline-4,4'-piperidin]-1-one
1'-phenethyl-2,3-dihydro-1H-spiro[isoquinoline-4,4'-piperidine]
2-methyl-1'-phenethyl-2,3-dihydro-1H-spiro[isoquinoline-4,4'-piperidine]
1-(1'-phenethyl-1H-spiro[isoquinoline-4,4'-piperidine]-2(3H)-yl)ethanone and
2-(2-hydroxyethyl)-1'-phenethyl-2,3-dihydro-1H-spiro[isoquinoline-4,4'-piperidin]-1-one.

16. A process for the preparation of the compound of Formula (I) according to claim 1,

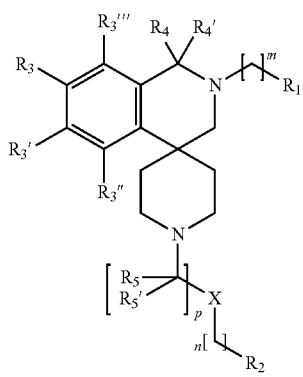

(I)

wherein said process comprises reacting a compound of Formula (IX')

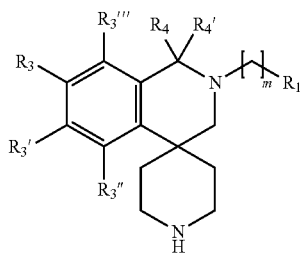

IX' with a compound of Formula (Xa) through a reductive amination reaction or (Xb) through an alkylation reaction

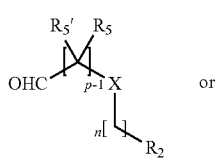

Xa

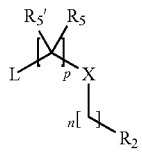

Xb said process comprises N-alkylating a compound of Formula (Ia')

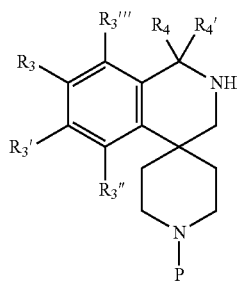

(Ia')

with a compound of Formula (VIa)

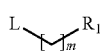

VIa wherein P is

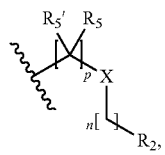

and L is a leaving group.

17. A pharmaceutical composition which comprises the compound according to claim 1, or a pharmaceutically acceptable salt thereof, and a pharmaceutically acceptable carrier, adjuvant or vehicle.

18. A method of treating pain in a subject in need thereof, comprising administration of an effective amount of the compound according to claim 1.

19. The method according to claim 18, wherein the pain is medium to severe pain, visceral pain, chronic pain, cancer pain, migraine, inflammatory pain, acute pain or neuropathic pain, allodynia or hyperalgesia.

20. The compound according to claim 1 which is in the form of an enantiomer, a diastereomer, or a mixture of enantiomers and/or diastereomers, in any mixing ratio.

21. The process according to claim 16, wherein L is chloro, bromo, mesylate, or tosylate.

* * * * *